(12) United States Patent
Morimoto

(10) Patent No.: US 10,478,152 B2
(45) Date of Patent: *Nov. 19, 2019

(54) ENDOSCOPE APPARATUS

(71) Applicant: FUJIFILM Corporation, Tokyo (JP)

(72) Inventor: Yasuhiko Morimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/860,954

(22) Filed: Sep. 22, 2015

(65) Prior Publication Data

US 2016/0089125 A1 Mar. 31, 2016

(30) Foreign Application Priority Data

Sep. 30, 2014 (JP) ................. 2014-202576

(51) Int. Cl.
*A61B 1/00* (2006.01)
*A61B 1/018* (2006.01)
(Continued)

(52) U.S. Cl.
CPC ............ *A61B 8/12* (2013.01); *A61B 1/00066* (2013.01); *A61B 1/00098* (2013.01);
(Continued)

(58) Field of Classification Search
CPC ... G02B 23/2476; A61B 8/12; A61B 1/00066; A61B 1/00098; A61B 8/445;
(Continued)

(56) References Cited

U.S. PATENT DOCUMENTS 5,882,293 A 3/1999 Ouchi
6,283,951 B1 * 9/2001 Flaherty ................. A61B 17/11
604/164.11
(Continued)

FOREIGN PATENT DOCUMENTS

CN 101011273 A 8/2007
JP 53-117236 U 9/1978
(Continued)

OTHER PUBLICATIONS

Japanese Office Action dated Dec. 2, 2016 in related Japanese Patent Application No. 2014-202576 with an English Translation.
(Continued)

*Primary Examiner* — John P Leubecker
*Assistant Examiner* — Genja M Frankert
(74) *Attorney, Agent, or Firm* — Birch, Stewart, Kolasch & Birch, LLP

(57) ABSTRACT

There is provided an endoscope apparatus in which a forceps elevator can be operated according to the operator's intention even when a treatment tool has large bending stiffness. The forceps elevator is erectably provided in a distal end part of the insertion part of the endoscope apparatus and guides the treatment tool led out from the distal end part. The forceps elevator has an erecting motion range from a minimum angular position to a maximum angular position. If a state in which the treatment tool is not led out from the distal end part is assumed, the erecting operation lever for operating the movement of the forceps elevator has: a first operation range where the erecting operation lever is operated within the erecting motion range of the forceps elevator; and a second operation range where the erecting operation lever is operated beyond the first operation range.

6 Claims, 32 Drawing Sheets

(51) Int. Cl.
  *A61B 8/12* (2006.01)
  *A61B 10/04* (2006.01)
  *A61B 17/00* (2006.01)
  *G02B 23/24* (2006.01)
  *A61B 8/08* (2006.01)
  *A61B 8/00* (2006.01)

(52) U.S. Cl.
  CPC ............. *A61B 8/0841* (2013.01); *A61B 8/445* (2013.01); *A61B 2010/045* (2013.01); *A61B 2017/0034* (2013.01); *G02B 23/2476* (2013.01)

(58) Field of Classification Search
  CPC .......... A61B 8/0841; A61B 2017/0034; A61B 2010/045; A61B 1/00149; A61B 1/018
  See application file for complete search history.

(56) References Cited

U.S. PATENT DOCUMENTS

| | | | |
|---|---|---|---|
| 7,641,480 B1 | 1/2010 | Hossack et al. | |
| 2001/0044570 A1* | 11/2001 | Ouchi | A61B 1/00098 600/107 |
| 2002/0091303 A1 | 7/2002 | Ootawara et al. | |
| 2002/0193741 A1* | 12/2002 | Secrest | A61B 1/00098 604/164.06 |
| 2003/0073955 A1* | 4/2003 | Otawara | A61B 1/00098 604/164.01 |
| 2004/0049095 A1* | 3/2004 | Goto | A61B 1/00098 600/107 |
| 2005/0049455 A1 | 3/2005 | Ootawara et al. | |
| 2005/0222493 A1 | 10/2005 | Kohno | |
| 2005/0228403 A1* | 10/2005 | Ho | A61B 10/0266 606/113 |
| 2007/0175949 A1* | 8/2007 | Shelton | A61B 17/07207 227/176.1 |
| 2007/0232857 A1* | 10/2007 | Otawara | A61B 1/00098 600/129 |
| 2007/0255103 A1 | 11/2007 | Maruyama | |
| 2007/0270638 A1* | 11/2007 | Kitano | A61B 1/00098 600/104 |
| 2010/0228086 A1* | 9/2010 | Ohki | A61B 1/00098 600/106 |
| 2011/0077461 A1* | 3/2011 | Maruyama | A61B 1/00098 600/107 |
| 2012/0078041 A1* | 3/2012 | Kitano | A61B 1/00098 600/107 |
| 2014/0221749 A1 | 8/2014 | Grant et al. | |
| 2015/0173711 A1* | 6/2015 | Hiraoka | A61B 8/445 600/466 |
| 2015/0182727 A1* | 7/2015 | Gurley | A61B 5/064 604/510 |
| 2016/0150946 A1* | 6/2016 | Tsumaru | A61B 1/00098 600/107 |
| 2016/0367114 A1* | 12/2016 | Iizuka | A61B 1/00 |
| 2017/0000316 A1* | 1/2017 | Sueyasu | F16H 35/18 |
| 2017/0020370 A1* | 1/2017 | Yamaya | A61B 1/00098 |

FOREIGN PATENT DOCUMENTS

| | | |
|---|---|---|
| JP | 61-15841 Y2 | 5/1986 |
| JP | 63-2007 Y2 | 1/1988 |
| JP | 5-56912 A | 3/1993 |
| JP | 5-344973 A | 12/1993 |
| JP | 2002-34905 A | 2/2002 |
| JP | 2003-116777 A | 4/2003 |
| JP | 2005-287593 A | 10/2005 |
| JP | 2007-289466 A | 11/2007 |
| JP | 2011-50643 A | 3/2011 |
| JP | 2011-072455 A | 4/2011 |

OTHER PUBLICATIONS

U.S. Office Action, dated Jan. 31, 2018, for copending U.S. Appl. No. 14/861,024.
Japanese Office Action and English translation, dated Nov. 25, 2016, for Japanese Application No. 2014-202579.
Japanese Office Action with English machine translation, dated Dec. 2, 2016, for Japanese Application No. 2014-202577.
U.S. Office Action from co-pending U.S. Appl. No. 14/861,024 dated Sep. 5, 2017.
Corrected Notice of Allowance for U.S. Appl. No. 14/861,024, dated Jun. 13, 2018.
Notice of Allowance for U.S. Appl. No. 14/861,024, dated May 25, 2018.
Office Action and Search Report dated May 20, 2019 in Chinese Patent Application No. 201510632838.7, with English translation.
Office Action and Search Report dated May 21, 2019 in Chinese Patent Application No. 201510632839.1, with English translation.
Chinese Office Action and Search Report dated Aug. 23, 2019 in counterpart Chinese Patent Application No. 201510633532.3, with English translation.

* cited by examiner

ENDOSCOPE APPARATUS

CROSS-REFERENCE TO RELATED APPLICATIONS

The patent application claims priority under 35 U.S.C. § 119 to Japanese Patent Application No. 2014-202576, filed on Sep. 30, 2014. Each of the above application(s) is hereby expressly incorporated by reference, in its entirety, into the present application.

BACKGROUND OF THE INVENTION

Field of the Invention

The present invention relates to an endoscope apparatus, and specifically, relates to an endoscope apparatus including an erecting operation member for erecting a forceps elevator (treatment tool elevator) of a distal end part a traction of an operation wire.

Description of the Related Art

In an ultrasonic inspection in an ultrasonic endoscope, tissue sampling and suction by a puncture needle are optionally performed under the ultrasonic endoscope.

A puncture needle is inserted from a treatment tool entry port of an ultrasonic endoscope and led out from a treatment tool exit port provided in the distal end part of the ultrasonic endoscope through a treatment tool insertion channel. A forceps elevator is provided in the treatment tool exit port, and the forceps elevator is configured so that it can move from a reclined state to an erected state by operating an erecting operation member and pulling an operation wire. By this means, the puncture needle which is led out from the treatment tool exit port becomes able to approach a body wall at a desired angle.

Japanese Patent Application Laid-Open No. 5-344973 discloses that stopper mechanism which restricts a maximum erecting angle of a forceps elevator is provided and a puncture needle led out from a treatment tool exit port is set so as to enter a favorable image range of an ultrasound probe by erecting the forceps elevator to the maximum erecting angle restricted by the stopper mechanism. Further, according to this configuration, Japanese Patent Application Laid-Open No. 5-344973 describes that a lead-out direction of the puncture needle is easily anticipated only by erecting the forceps elevator up to the angle restricted by the stopper mechanism, and, since a lead-out angle of the puncture needle is not likely to vary, it is possible to safely perform puncturing under ultrasonic guide.

SUMMARY OF THE INVENTION

Since the above-mentioned puncture needle has high bending stiffness and is hard due to its structure, in a case where a forceps elevator is set to a maximum erecting angle (a maximum angular position in an erecting motion range) and the puncture needle is led out, a large force is applied to the forceps elevator toward a reclining direction because the puncture needle tries to return to a straight shape.

Therefore, if an operator tries to set the forceps elevator to the maximum angular position in the erecting motion range like Japanese Patent Application Laid-Open No. 5-344973, there is a problem that the forceps elevator cannot be set to the maximum angular position due to, for example, slight extension of a wire and so on, even though the erecting operation member is maximally operated toward the erecting side. Moreover, since the bending stiffness generally becomes larger as the outer diameter of a penetration needle becomes larger (thicker), the phenomenon that the forceps elevator cannot be set to the maximum angular position becomes remarkable when a puncture needle having a large outer diameter is used.

In addition, not only for an ultrasonic endoscope, further, not only for a puncture needle, whenever a treatment tool having large bending stiffness is used in an endoscope, since the fact that the forceps elevator cannot be erected to the maximum angular position leads to reduction in the erecting motion range of the forceps elevator, there is a problem of causing the degradation of operability.

The present invention is made considering such circumstances, and aims to provide an endoscope apparatus in which a forceps elevator can be operated as intended by an operator even when a treatment tool having large bending stiffness is erected.

To achieve the above-mentioned object, an endoscope apparatus according to an aspect of the present invention includes: an insertion part configured to be inserted in an inside of a body; an operation part continuously provided on a proximal end side of the insertion part; a forceps elevator which is erectably provided to a distal end part of the insertion part, has an erecting motion range from a minimum angular position to a maximum angular position, and is configured to guide a treatment tool led out from the distal end part; an operation wire whose one end is coupled with the forceps elevator and which is inserted into the insertion part; and an erecting operation member which is provided to the operation part, with which another end of the operation wire is coupled, and which is configured to erect the forceps elevator by pulling the operation wire, wherein if a state in which the treatment tool is not led out from the distal end part is assumed, the erecting operation member has: a first operation range in which the operation wire is pulled within the erecting motion range of the forceps elevator; and a second operation range in which the operation wire is further pulled when the erecting operation member is greatly pulled beyond the first operation range.

According to the aspect of the present invention, in a state in which the treatment tool is not led out from the distal end part, the endoscope apparatus has the second operation range in which the operation wire can be greatly pulled, compared to the first operation range which is sufficient to erect the forceps elevator from the minimum angular position to the maximum angular position. Thus, it is possible to erect the forceps elevator to the maximum angular position by performing an operation in the second operation range even when the forceps elevator cannot be erected to the maximum erecting angle only by an operation in the first operation range, at the time of erecting a treatment tool having large bending stiffness.

In an endoscope apparatus according to the aspect of the present invention, it is desirable to adopt a mode in which when it is assumed that an entire operation range of the erecting operation member is formed with the first operation range and the second operation range, the first operation range is equal to or greater than 40% of the entire operation range of the erecting operation member and equal to or less than 70% thereof.

In an endoscope apparatus according to the aspect of the present invention, it is possible to adopt a mode in which the operation part includes an index configured to identify whether an operation range of the erecting operation member is in the first operation range or in the second operation range.

According to this mode, in a case where the treatment tool is not led out from the distal end part or in a case where a treatment tool having small bending stiffness is led out, an operator can recognize whether or not the forceps elevator is set in the maximum angular position.

In an endoscope apparatus according to the aspect of the present invention, it is possible to adopt a mode in which the operation part includes an index which is shielded by the erecting operation member when the forceps elevator is in the minimum angular position, and which is exposed when the forceps elevator is in a position in which the forceps elevator is erected from the minimum angular position.

According to this mode, it is possible to urge an operator to recline the forceps elevator in a case where the operator unintentionally erects the forceps elevator. Moreover, such the mode can be realized at a low cost because it has a simple configuration using the operation state of the erecting operation member.

In an endoscope apparatus according to the aspect of the present invention, it is possible to adopt a mode where there is provided a bending operation knob which is rotatably arranged to the operation part and is configured to perform a bending operation of a bending part provided on a distal end side of the insertion part, and the erecting operation member is rotatably arranged on a same axis as a rotation axis of the bending operation knob.

According to the present invention, it is possible to operate a forceps elevator according to the operator's intention even in a case where a treatment tool having large bending stiffness is erected.

DETAILED DESCRIPTION OF THE EMBODIMENTS

In the following, preferable embodiments of the present invention are described in detail according to the accompanying drawings.

Figure 1:
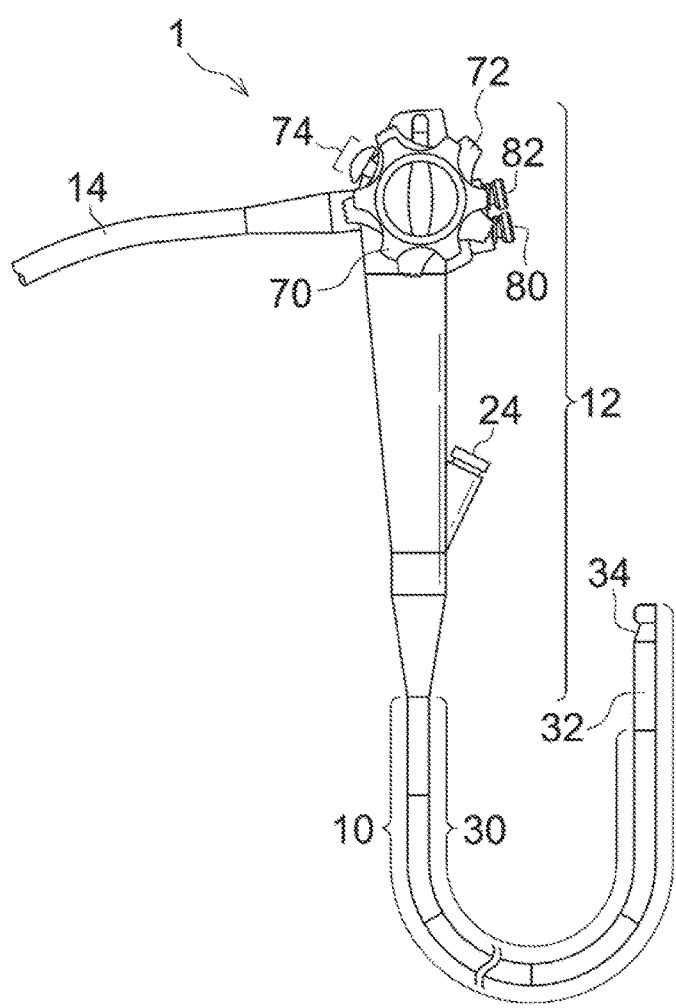
FIG. 1 is a schematic diagram of an ultrasonic endoscope according to an embodiment of an endoscope apparatus to which the present invention is applied.

FIG. 1 is a schematic diagram of an ultrasonic endoscope 1 that is an embodiment of an endoscope apparatus to which the present invention is applied.

The ultrasonic endoscope 1 (which is simply called an endoscope 1 below) is includes: an insertion part 10 which is to be inserted in the inside of a subject's body; an operation part 12 which is continuously provided on the proximal end side of the insertion part 10 and which is to be holed by an operator to perform various operations; and a universal cord 14 which is continuously provided in the operation part 12 and connects the endoscope 1 with system configuration apparatuses which are constituting an endoscope system such as an unillustrated processor apparatus and a light source apparatus.

The insertion part 10 is formed into a long shape with a narrow diameter as a whole and is configured by continuously arranging a flexible part 30 having flexibility, a bending part 32 which is bendable by an operation of the operation part 12, and a distal end part 34 in which an imaging apparatus, an ultrasonic transducer (electromagnetic acoustic transducer) and so on are disposed, in this order from the proximal end side to the distal end side.

Various operating members to be operated by an operator are provided in the operation part 12, and, as described later, a right-and-left angle knob 70 and an up-and-down angle knob 72 which are bending operation knobs, an erecting operation lever 74 which is an erecting operation member, an air and water supply button 80 and a suction button 82, and so on, are provided.

Moreover, the operation part 12a includes treatment tool entry port 24 through which a treatment tool is inserted into a treatment tool insertion path (treatment tool insertion channel) which passes through the insertion part 10.

The universal cord 14 internally includes an electric cable, a light guide and a fluid tube. A connector is provided in an unillustrated end part of this universal cord 14. The connector is connected with the predetermined system configuration apparatus forming the endoscope system such as the processor apparatus and the light source apparatus, and thus, the power, a control signal, illumination light and liquid/gas, and so on, which are necessary for the operation of the endoscope 1, are supplied from the system configuration apparatus to the endoscope 1. Moreover, observation image data acquired by the imaging apparatus of the distal end part 34 and ultrasonic image data acquired by the ultrasonic transducer are transmitted from the endoscope 1 to the system configuration apparatuses. Here, the observation image and the endoscope image, which are transmitted to the system configuration apparatuses, are displayed on a monitor.

Figure 2:
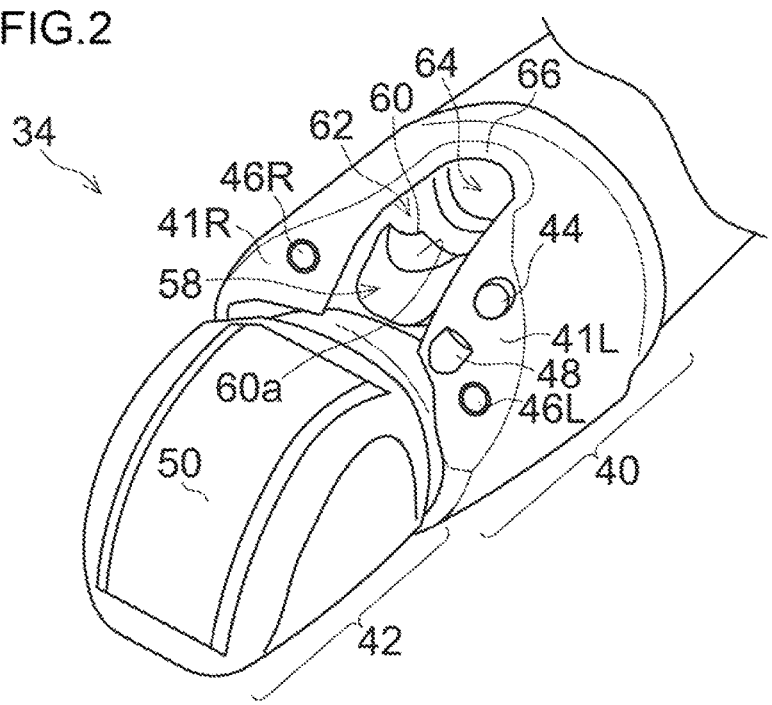
FIG. 2 is an expanded perspective view illustrating a distal end part.

FIG. 2 is an expanded perspective view illustrating the distal end part 34. As illustrated in the figure, the distal end part 34 includes a base part 40 disposed on the proximal end side and an extension part 42 which extends from the base part 40 provided on the distal end side.

A convex-type ultrasonic transducer 50 in which many ultrasonic vibrators that transmit and receive ultrasonic waves are disposed along an arc-shaped ultrasonic wave transmission and reception surface is disposed in the extension part 42. By this means, an ultrasound image (tomographic image) in a scanning surface parallel to the axis of the insertion part 10 is acquired by the ultrasonic transducer 50 and data of the image are transmitted to the system configuration apparatuses connected with the universal cord 14 through a signal cable inserted inside the insertion part 10, the operation part 12 and the universal cord 14.

In the base part 40, an observation window 44, an air and water supply nozzle 48 and an illumination window 46L are provided in a left side slope 41L facing obliquely upward on the distal end side, and an illumination window 46R is provided in a right side slope 41R directed obliquely upward on the distal end side. The treatment tool exit part 58 is provided in the central part between the left side slope 41L and the right side slope 41R.

An imaging apparatus in which an image formation optical system and a solid imaging element are integrally assembled is disposed inside the base part 40 that is the proximal end side of the observation window 44. By this means, light from a site to be observed that is the visual field range of an imaging unit is collected from the observation window 44, an optical image of the site to be observed is formed by the image formation optical system, and the optical image is converted into an electrical signal by the solid imaging element. Further, the observation image data converted into the electrical signal is transmitted to the system configuration apparatuses connected with the universal cord 14 through the signal cable inserted inside the insertion part 10, the operation part 12 and the universal cord 14.

A light emitting unit is disposed inside the base part 40 that is the proximal end side of each of the illumination windows 46R and 46L. Illumination light is led out from the system configuration apparatuses connected with the universal cord 14 through the light guide inserted inside the insertion part 10, the operation part 12 and the universal cord 14 to the light emitting unit. The illumination light is emitted from the light emitting unit through the illumination windows 46R and 46L to irradiate the site to be observed.

An air and water supply nozzle 48 is connected with the system configuration apparatuses connected with the universal cord 14 through a fluid tube inserted inside the insertion part 10, the operation part 12 and the universal cord 14. The gas or water supplied from the system configuration apparatus is jetted from the air and water supply nozzle 48 toward the observation window 44 and the washing or the like of the observation window 44 is performed.

The treatment tool exit part 58 has a concave treatment tool erecting space 62, and a treatment tool exit port 64 is disposed on the proximal end side of the treatment tool erecting space 62.

The treatment tool exit port 64 is coupled with the treatment tool entry port 24 of the operation part 12 (see FIG. 1) through the treatment tool insertion path (treatment tool insertion channel) passing through the insertion part 10, and a treatment tool inserted from the treatment tool entry port 24 is led out from the treatment tool exit port 64 to the treatment tool erecting space 62.

Moreover, in the treatment tool erecting space 62, a forceps elevator 60 is disposed on the distal end side with respect to (closer to the distal end than) the treatment tool exit port 64.

The forceps elevator 60 has a concave guide surface 60a bended upward from the proximal end side to the distal end side on the upper surface side, and the treatment tool led out from the treatment tool exit port 64 abuts on the guide surface 60a of the forceps elevator 60 and bends upward. By this means, the treatment tool led out from the treatment tool exit part 58 of the distal end part 34, that is, the treatment tool led out from an opening part 66 of the treatment tool erecting space 62 is protrusively disposed (disposed so as to protrude) along an oblique upward direction from the proximal end side to the distal end side with respect to the central axis (the longitudinal axis of the insertion part 10) that passes through the center of the distal end part 34, by the forceps elevator 60.

Figure 3:
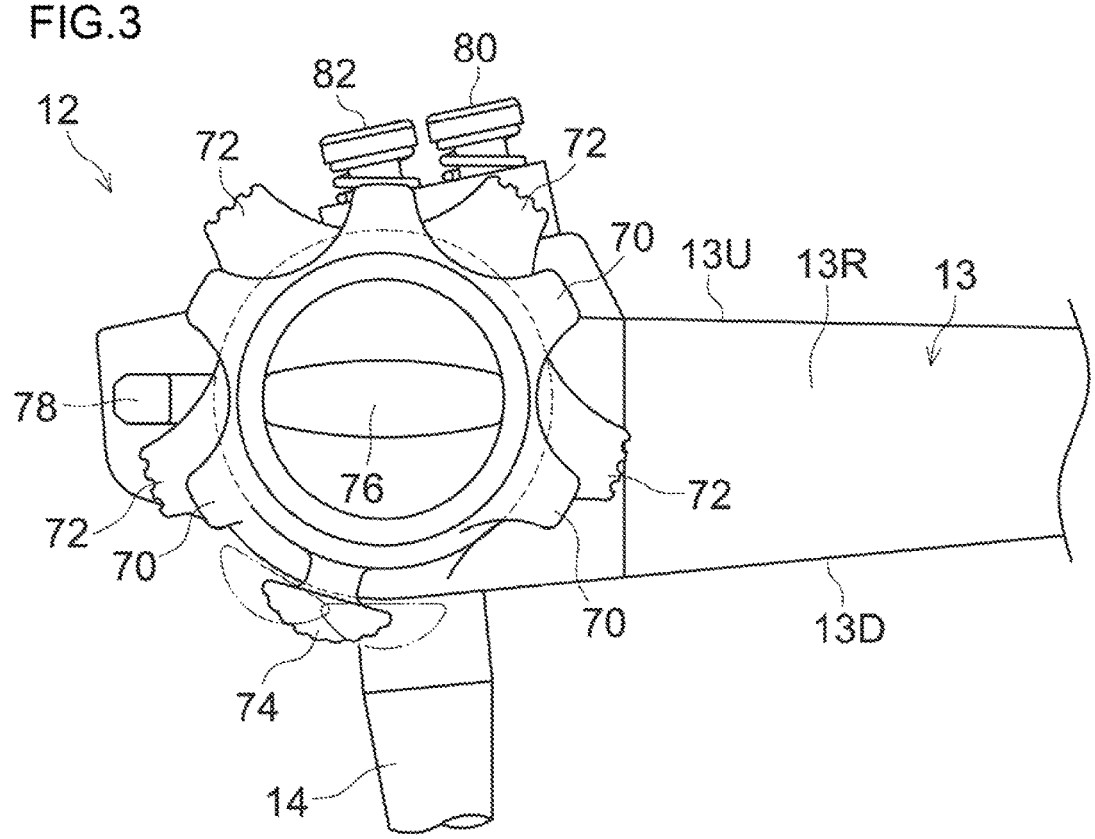
FIG. 3 is an expanded side view illustrating an operation part.
Figure 4:
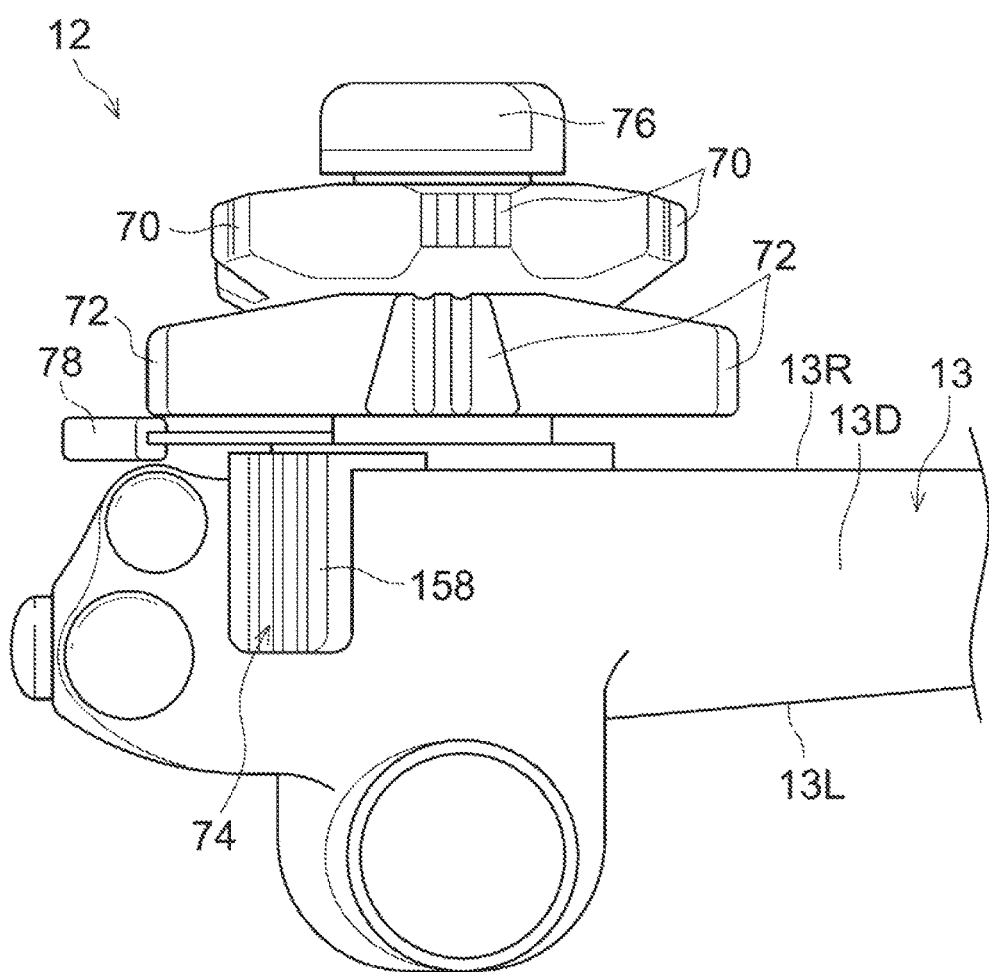
FIG. 4 is an expanded bottom view illustrating the operation part.

FIGS. 3 and 4 are an expanded side and an expanded bottom view illustrating the operation part 12.

As illustrated in these figures, the operation part 12 is covered with a casing 13 which is an operation part body that defines the inside and outside of the operation part 12. In a right side surface 13R of the operation part 12 formed by the casing 13, a right-and-left angle knob 70, an up-and-down angle knob 72, an erecting operation lever 74, a right-and-left lock knob 76 and an up-and-down lock lever 78, and so on, are provided.

Figure 32:
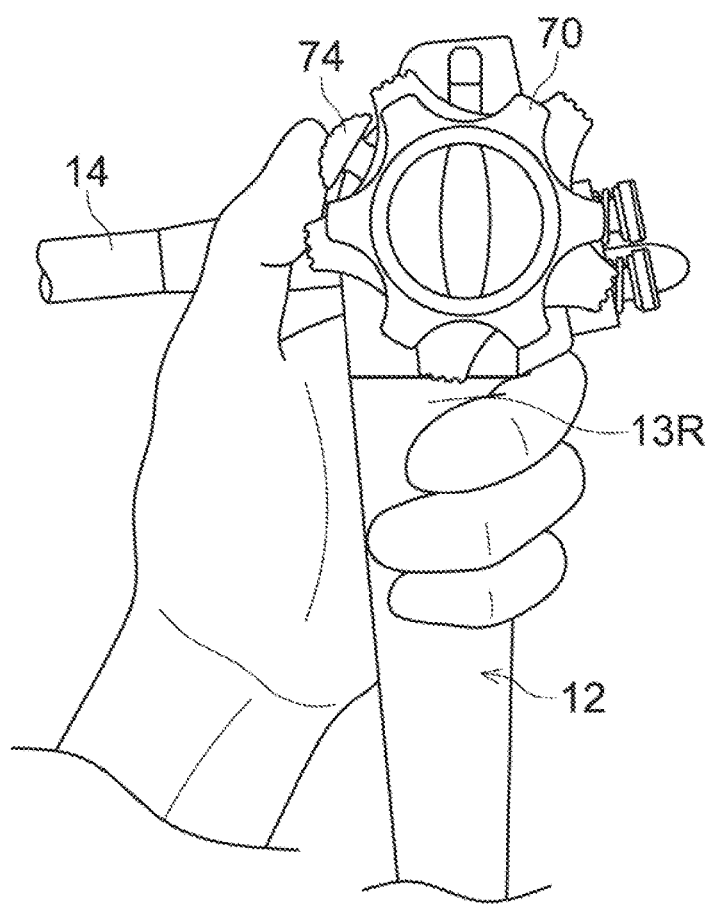
FIG. 32 is a diagram illustrating a state where the operation part is held with a general method and the erecting operation lever is operated when an endoscope is operated.

Here, normally, when operating the endoscope 1, as illustrated in FIG. 32, an operator (operating person) holds the operation part 12 by the left hand while turning the distal end side of the operation part 12 (the side of the insertion part 10) to the bottom and turning the proximal end side which is the opposite side to the top, and then holds the operation part 12 such that the palm of the left hand faces the side of the left side surface 13L which is the side opposite to the right side surface 13R in which the right-and-left angle knob 70 or the like is disposed, an upper surface 13U is caught with other fingers than the thumb and a lower surface 13D is caught with the thumb. In this case, the upper surface 13U of the operation part 12 faces the front side, and a lower surface 13D of the operation part 12 faces the rear side (operator side), as seen from the operator.

The right-and-left angle knob 70, the up-and-down angle knob 72, the erecting operation lever 74, the right-and-left lock knob 76 and the up-and-down lock lever 78 of the operation part 12 are provided so as to be rotatable around an axis which is substantially orthogonal to the right side surface 13R. When the right-and-left angle knob 70 and the up-and-down angle knob 72 are rotated, the bending part 32 is bended in the right-and-left direction and the up-and-down direction. When the right-and-left lock knob 76 and the up-and-down lock lever 78 are rotated, the rotational positions of the right-and-left angle knob 70 and the up-and-down angle knob 72 are locked or the lock is released.

When the erecting operation lever 74 is rotated, it works in directions in which the forceps elevator 60 in the distal end part 34 erects or reclines, and the angular position (erecting angle) of the forceps elevator 60 is varied, as described later in detail. By this means, the lead-out direction (lead-out angle) of the treatment tool led out from the distal end part 34 (the treatment tool exit part 58) is varied.

Figure 33:
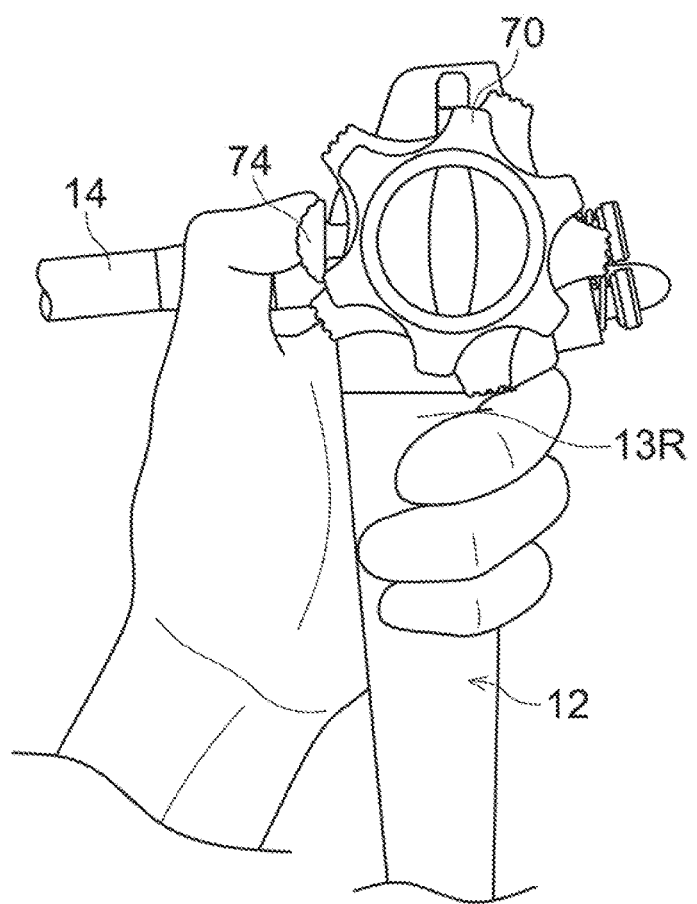
FIG. 33 is a diagram illustrating a state where the operation part is held with a general method and the erecting operation lever is operated when the endoscope is operated.

Here, the erecting operation lever 74 is operated by the thumb as illustrated in FIGS. 32 and 33.

Moreover, the air and water supply button 80, the suction button 82, and so on, are provided in the upper surface 13U of the operation part 12 as illustrated in FIG. 3. The jet of gas or water from the air and water supply nozzle 48 in the distal end part 34 can be turned on or off by operating the air and water supply button 80. Suction from the treatment tool exit part 58 can be turned on or off through a suction channel coupled with a treatment tool insertion path by operating the suction button 82.

Next, a forceps elevator drive mechanism which erects or reclines the forceps elevator 60 of the distal end part 34 by the operation of the erecting operation lever 74 of the operation part 12 is described. Here, in this specification, the erecting motion and reclining motion of the forceps elevator 60 are collectively called erecting motion.

Figure 5:
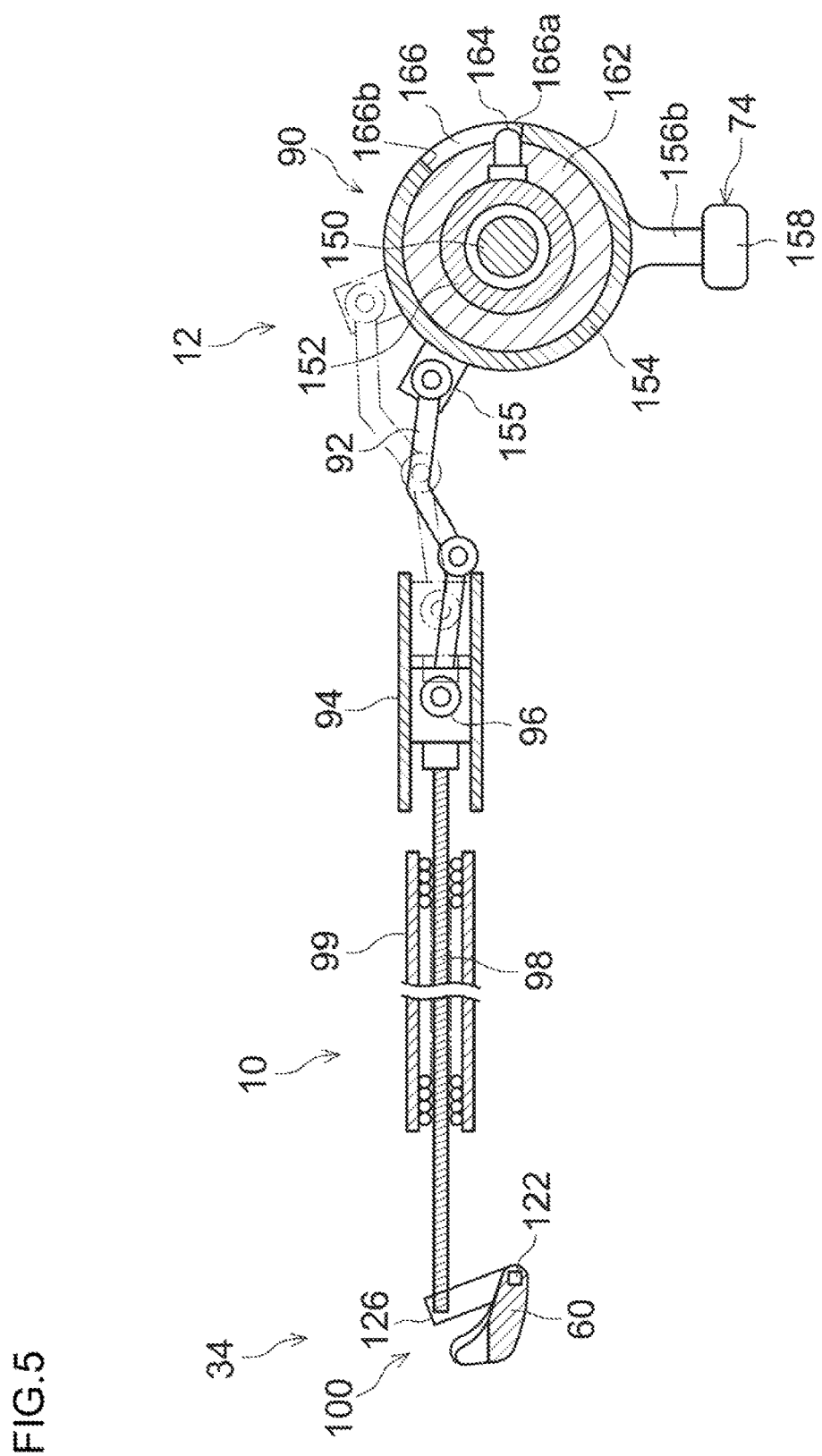
FIG. 5 is a configuration diagram simply illustrating the entire configuration of a forceps elevator drive mechanism.

FIG. 5 is a configuration diagram simply illustrating the whole configuration of the forceps elevator drive mechanism.

As illustrated in the figure, in the operation part 12, one end of a crank member 92 is rotatably coupled with the erecting operation lever 74 through a below-mentioned operation-part power transmission mechanism 90 disposed in the operation part 12. A slide 96 which is supported by a slide guide 94 movably forward and backward is coupled with the other end of the crank member 92 so as to be rotatable with respect to the crank member 92. By this means, the slider 96 moves forward and backward by the operation (movement) of the erecting operation lever 74.

The proximal end of an operation wire 98 is fixed to the slider 96. The operation wire 98 is inserted from the inside of the operation part 12 and extends through the inside of the insertion part 10, up to the distal end part 34. Here, the operation wire 98 is disposed inside the insertion part 10 to pass through a wire guide tube 99 such as a contact coil so as to be able to move forward and backward.

Further, in the distal end part 34, the forceps elevator 60 is coupled with the distal end of the operation wire 98 through a distal-end-part power transmission mechanism 100 described below. The proximal end side of the forceps elevator 60 is supported to be rotatable with respect to the distal end part 34.

By this means, when the operation wire 98 moves forward and backward by the forward and backward movement of the slider 96, the distal end side of the forceps elevator 60 is rotated around the proximal end side to erect the forceps elevator 60.

As mentioned above, it is configured such that the power applied to the erecting operation lever 74 by the operation of an operator is transmitted to the forceps elevator 60 through the operation-part power transmission mechanism 90, the crank member 92, the operation wire 98 and the distal-end-part power transmission mechanism 100, so as to allow the forceps elevator 60 to be erected.

Figure 6:
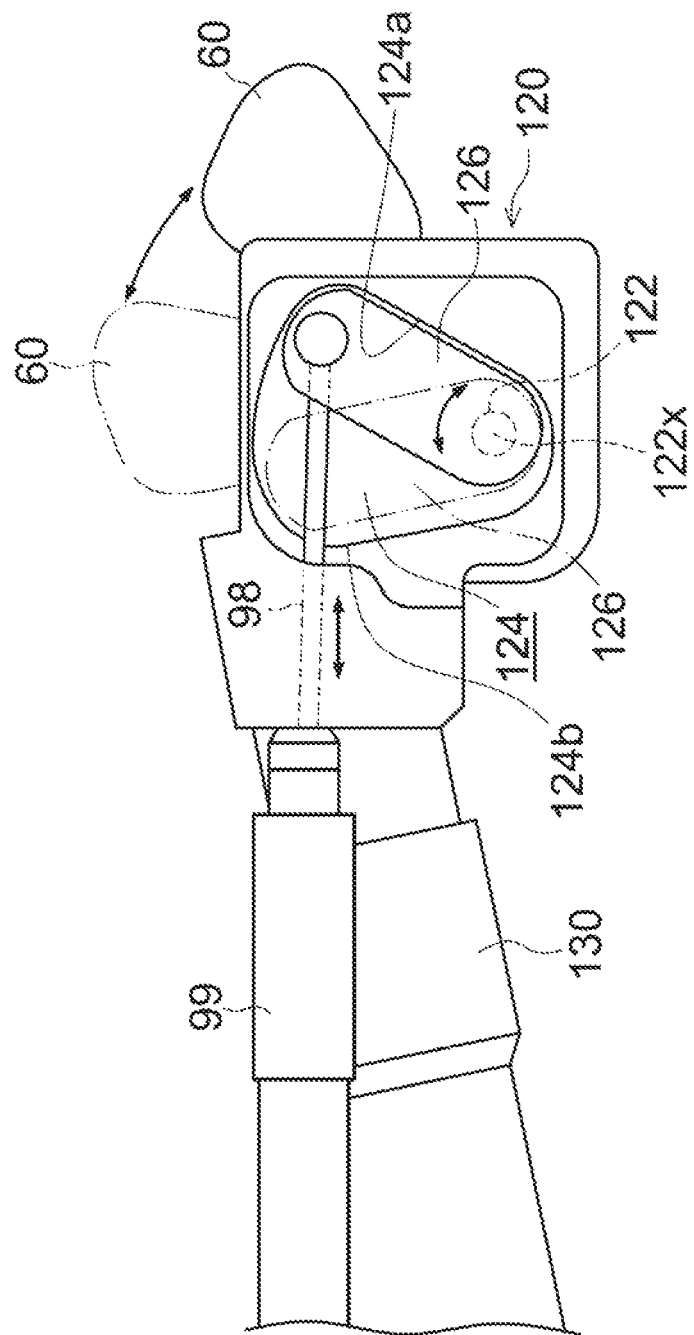
FIG. 6 is a configuration diagram simply illustrating a power transmission mechanism in a distal end part.

Next, an embodiment of the distal-end-part power transmission mechanism 100 in FIG. 5 is described. FIG. 6 is a configuration diagram simply illustrating the distal-end-part power transmission mechanism 100. In the distal end part 34, a lever housing body 120 in FIG. 6, which forms a part of a side surface on the right side, is arranged in a position facing a wall surface on the right side of the treatment tool erecting space 62 of the treatment tool exit part 58 illustrated in FIG. 2.

The lever housing body 120 has a wall part forming the wall surface on the right side of the treatment tool erecting space 62, a rotating shaft member 122 is rotatably supported while penetrating the wall part. One end part of the rotating shaft member 122 projects to the treatment tool erecting space 62 and the other end part projects to a lever housing space part 124 formed inside the lever housing body 120.

Further, the end part on the proximal end side of the forceps elevator 60 is fixed to the end part that projects to the treatment tool erecting space 62 of the rotating shaft member 122 (see FIG. 5). On the other hand, an end part on the proximal end side of a erecting lever 126 housed in the lever housing space part 124 is fixed to the end part that projects to the lever housing space part 124 of the rotating shaft member 122. The tip end of the operation wire 98 is rotatably coupled with an end part on the distal end side of the erecting lever 126 (through a connection pin rotatable with respect to the erecting lever 126) (see FIG. 5).

By this means, when the operation wire 98 moves forward and backward by the operation of the erecting operation lever 74 of the operation part 12, the erecting lever 126 rotates around an axis 122x passing through the center of the rotating shaft member 122 together with the rotating shaft member 122. Further, the forceps elevator 60 rotates around the axis 122x together with the rotating shaft member 122 by the rotation of the rotating shaft member 122 and is subjected to erecting motion.

Here, in FIG. 6, the front end of the wire guide tube 99 which is illustrated in FIG. 5 and through which the operation wire 98 is inserted is fixed to the proximal end side of the lever housing body 120. Moreover, a tube member 130 in the figure is a member forming a treatment tool insertion channel, and it is connected so as to communicate with the treatment tool entry port 24 (see FIG. 2).

Moreover, the distal-end-part power transmission mechanism 100, which transmits the power by the forward and backward movement of the operation wire 98 as a power to erect the forceps elevator 60, is not limited to the configuration of the above-mentioned embodiment, and an arbitrary configuration can be adopted. For example, a configuration in which the tip of the operation wire 98 is directly coupled with the forceps elevator 60 may be possible, or a configuration in which the operation wire 98 is indirectly coupled with the forceps elevator 60 by a configuration different from the above-mentioned embodiment may be possible.

Figure 7:
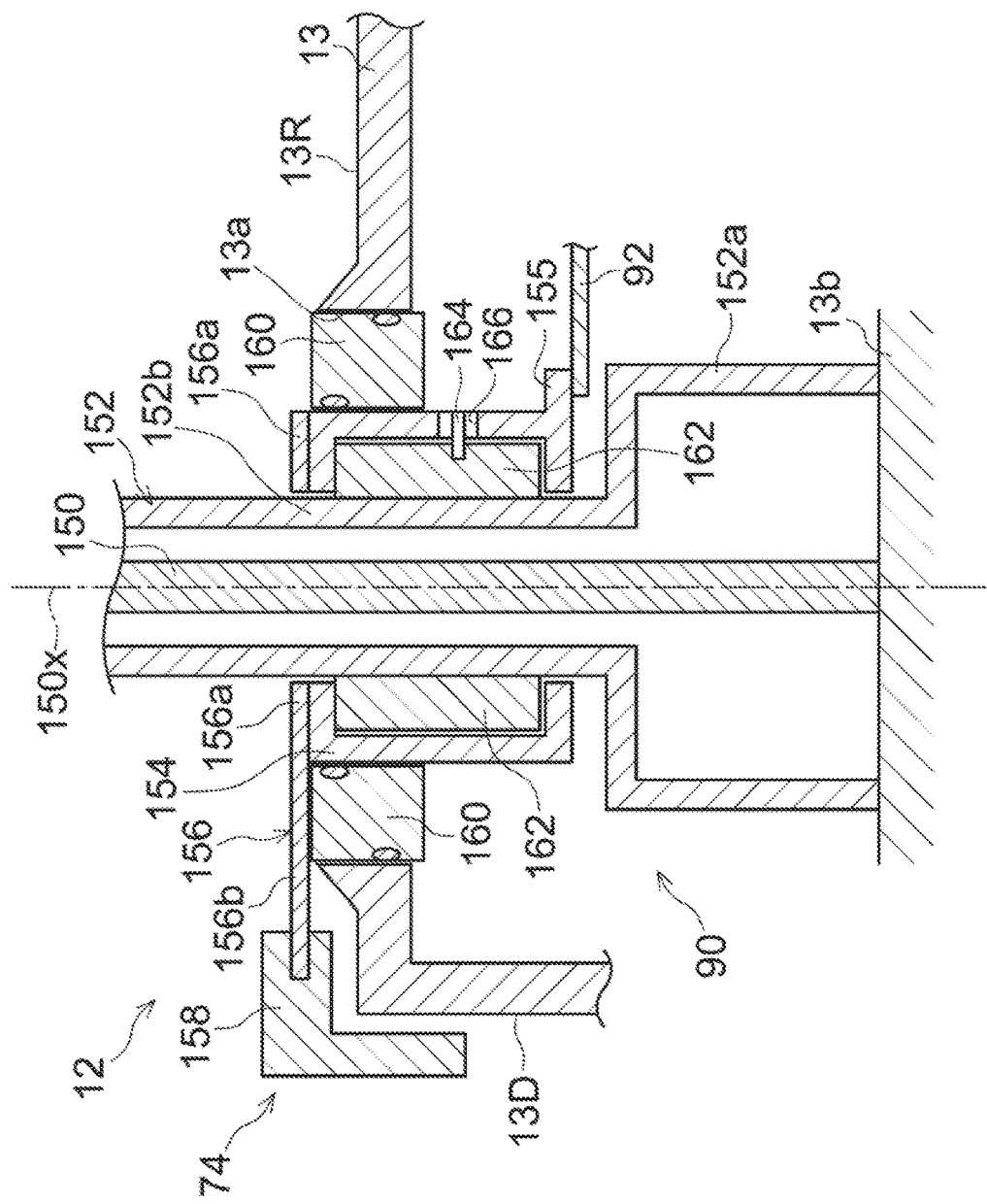
FIG. 7 is a configuration diagram simply illustrating a power transmission mechanism in an operation part.

Next, an embodiment of the operation-part power transmission mechanism 90 in FIG. 5 is described. FIG. 7 is a configuration diagram simply illustrating the operation-part power transmission mechanism 90. As illustrated in the figure, a through hole 13a which communicates the inside and outside of the casing 13 is formed in a part in which the right side surface 13R (see FIGS. 3 and 4) of the casing 13 that is an operation part main body of the operation part 12. In the through hole 13a, a columnar main shaft 150 and a cylindrical fixing shaft 152 (see FIG. 5) which extend from the inside to the outside of the casing 13 and which are substantially orthogonal to the right side surface 13R are provided on the same axis along an axis 150x.

Regarding these main shaft 150 and fixing shaft 152, one end parts (end parts on the proximal end side) are fixed to a support part 13b which is a part of the casing 13 or a part of a member fixed to the casing 13, in the inside of the casing 13.

Here, there is a space between the outer peripheral surface of the main shaft 150 and the inner peripheral surface of the fixing shaft 152, and an unillustrated power transmission mechanism is disposed between them, where the power transmission mechanism transmits the power by respective rotation operations of the right-and-left angle knob 70 and the up-and-down angle knob 72 which are illustrated in FIGS. 3 and 4, to a right-and-left operation wire which bends the bending part 32 in the right and left direction and an up-and-down operation wire which bends the bending part 32 in the upper and lower direction respectively.

For example, the fixing shaft 152 includes a large diameter part 152a and a small diameter part 152b, in which the diameter on the proximal end side is expanded more than the distal end side. On the inner peripheral surface side of the large diameter part 152a, two pulleys, which rotate around the main shaft 150 and wind and pull each of the right-and-left operation wire and the up-and-down operation wire, are disposed. Further, respective cylindrical double rotation shafts are coupled with those respective pulleys, and those rotation shafts are inserted between the outer peripheral surface of the main shaft 150 and the inner peripheral surface of the fixing shaft 152, and coupled with the right-and-left angle knob 70 and the up-and-down angle knob 72 respectively. Here, the right-and-left angle knob 70 and the up-and-down angle knob 72 are supported so as to be rotatable around the axis 150x.

In the outer peripheral part of the small diameter part 152b of the fixing shaft 152, a cylindrical rotating drum 154 (see FIG. 5) is supported so as to rotatable around the fixing shaft 152 (around the axis 150x). An annular frame member 160 fixed to the casing 13 is disposed between the outer peripheral surface of the rotating drum 154 and the inner peripheral surface of the through hole 13a of the casing 13. An O-ring (O-ring) which is mounted to the inner peripheral surface and outer peripheral surface of the frame member 160 presses against the outer peripheral surface of the rotating drum 154 and the inner peripheral surface of the through hole 13a, and the space between the rotating drum 154 and the casing 13 is sealed. Here, the frame member 160 may be a part which is formed integrally with the casing 13 as a part of the casing 13.

A coupling member 156 includes an annular fixed part 156a and an arm part 156b (see FIG. 5) which extends from a part of the fixed part 156a in the radial direction is fixed to one end part (an end part on the distal end side) of this, rotating drum 154 by a screw, and so on. A finger hook part 158 (see FIG. 5) is fixed to the distal end part of the arm part 156b of the coupling member 156. The erecting operation lever 74 is formed with the arm part 156b and the finger hook part 158. By this means, the erecting operation lever 74 is disposed so as to be rotatable around the axis 150x in a position along the right side surface 13R outside the operation part 12.

Here, the finger hook part 158 of the erecting operation lever 74 has a bent shape and is disposed so as to extend from a position facing the right side surface 13R of the operation part 12 (casing 13) to a position facing the lower surface 13D.

On the other hand, a convex part 155 that projects in the radial direction is provided in the other end part (the end part on the proximal end side) of the rotating drum 154, and one end of the above-mentioned crank member 92 (see FIG. 5) is coupled with the convex part 155 so as to be rotatable.

By this means, when the erecting operation lever 74 rotated around the axis 150x, an end part of the crank member 92 rotates around the axis 150x together with the rotating drum 154. The slider 96 in FIG. 5 moves forward and backward by the rotation of the end part of this crank member 92, and the forceps elevator 60 is erected and reclined through the operation wire 98 and the distal-end-part power transmission mechanism 100.

Here, a mechanism that transmits the power applied to the erecting operation lever 74 to the operation wire 98 is not necessarily be formed with the operation-part power transmission mechanism 90 and the crank member 92, and so on, in the present embodiment. Moreover, the erecting operation lever 74 of the present embodiment is rotatably disposed on the same axis as the right-and-left angle knob 70 and the up-and-down angle knob 72 and performs rotation movement, but it may be a mechanism which includes the erecting operation lever 74 so as to be freely movable straight and transmits the power of the straight movement to the operation wire 98.

Next, the relationship between an operation range of the erecting operation lever 74 and an erecting motion range of the forceps elevator 60 is described.

As illustrated in FIGS. 5 and 7, a cylindrical restriction drum 162 fixed to the fixing shaft 152 is disposed inside the rotating drum 154, and a stopper member 164 that projects from the outer peripheral surface is fixed to the restriction drum 162. This stopper member 164 is inserted and disposed in a long groove 166 formed along the circumferential direction in a partial range of the peripheral wall part of the rotating drum 154.

By this means, a rotation angle range in which the rotating drum 154 is rotatable around the axis 150$x$ is restricted to a rotation angle range from a rotation angle when one end part 166$a$ (see FIG. 5) of the long groove 166 abuts on the stopper member 164 to a rotation angle when the other end part 166$b$ (see FIG. 5) abuts on the stopper member 164.

Further, a rotation angle range in which the erecting operation lever 74 can be subjected to a rotation operation, that is, an operation range in which the erecting operation lever 74 can be operated is also restricted to the rotation angle range in which the rotating drum 154 is rotatable.

Here, the position of the erecting operation lever 74 when the erecting operation lever 74 moves to a position at a rotation angle θ1 around the axis 150$x$ is expressed as an angular position θ1. Moreover, when the rotation angle range in which the erecting operation lever 74 is rotatable, that is, the operation range in which it can be operated, is assumed as the entire operation range, the angular position θ1 of the erecting operation lever 74 when the end part 166$a$ of the rotating drum 154 abuts on the stopper member 164 is expressed by θ1min as a minimum angular position of the entire operation range, and the angular position θ1 of the erecting operation lever 74 when the end part 166$b$ of the rotating drum 154 abuts on the stopper member 164 is expressed by θ1max (>θ1min) as a maximum angular position of the entire operation range.

Figure 8:
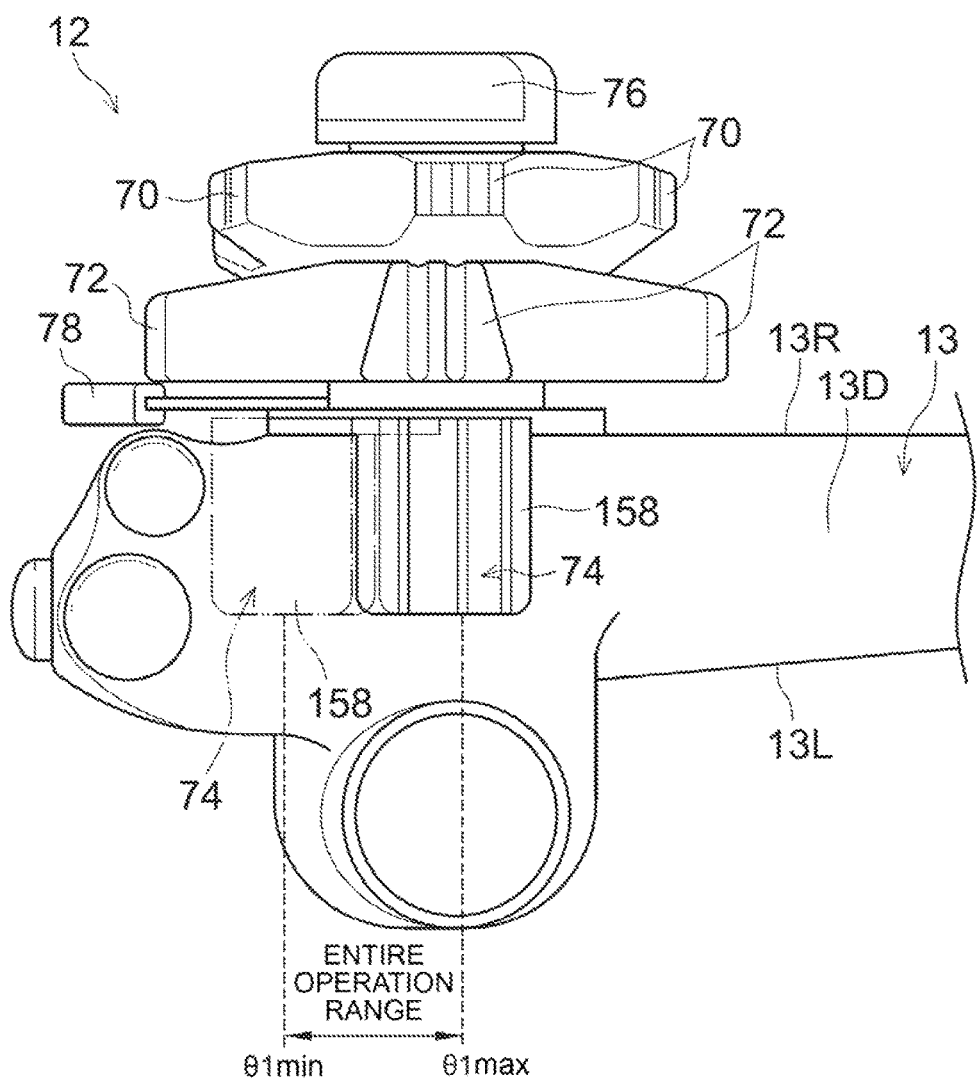
FIG. 8 is an expanded bottom view illustrating the operation part.

At this time, like the enlarged view in FIG. 8 illustrating the operation part 12 from the lower surface 13D in the same way as FIG. 4, the erecting operation lever 74 (finger hook part 158) is in a proximal end position on the most proximal end side in the entire operation range when the angular position θ1 is the minimum angular position θ1min. And, the erecting operation lever 74 is in a distal end position on the most distal end side in the entire operation range when the angular position θ1 is the maximum angular position θ1max. The erecting operation lever 74 moves within a range from the proximal end position to the distal end position.

Moreover, the operation wire 98 moves forward to the most distal end side when the erecting operation lever 74 is in the proximal end position (minimum angular position θ1min) in the entire operation range, that is, when the end part 166$a$ of the long groove 166 of the rotating drum 154 abuts on the stopper member 164 in FIG. 5, and the operation wire 98 moves backward to the most proximal end side when the erecting operation lever 74 is in the distal end position (maximum angular position θ1max) in the entire operation range, that is, when the end part 166$b$ of the long groove 166 of the rotating drum 154 abuts on the stopper member 164 in FIG. 5.

Therefore, the operation wire 98 can be moved backward to the proximal end side by moving the erecting operation lever 74 from the proximal end position to the distal end position in the entire operation range to increase the angular position θ1 of the erecting operation lever 74.

Here, the operation range of the erecting operation lever 74 may be restricted by any device in the operation part 12, and it is not limited to restriction by making the stopper member 164 abut on the long groove 166 of the rotating drum 154 like the present embodiment. For example, it is also possible to adopt a mode in which the operation range of the erecting operation lever 74 is directly restricted by a stopper member which abuts on the erecting operation lever 74, and so on. Moreover, it is also possible to adopt a mode in which the operation range of the erecting operation lever 74 is restricted by restricting the motion range of an arbitrary member that moves in interlock with the erecting operation lever 74 in the operation-part power transmission mechanism 90 of an arbitrary mode.

On the other hand, in FIG. 6, the erecting lever 126 coupled with the forceps elevator 60 through the rotating shaft member 122 rotates around the axis 122$x$ that pass through the center of the rotating shaft member 122. A rotation angle range in which the erecting lever 126 is rotatable around the axis 122$x$ is restricted to a rotation angle range from a rotation angle when the erecting lever 126 abuts on a wall surface 124$a$ on the distal end side on which the lever housing space part 124 of the lever housing body 120 is defined to a rotation angle when the erecting lever 126 abuts on a wall surface 124$b$ on the proximal end side on which the lever housing space part 124 is defined.

By this means, the rotation angle range in which the forceps elevator 60 is rotatable, that is, the erecting motion range of the forceps elevator 60 is restricted to the rotation angle range in which the erecting lever 126 is rotatable.

Here, the position of the forceps elevator 60 when the forceps elevator 60 is set to a position at a rotation angle θ2 around the axis 122$x$ is expressed as an angular position θ2. Moreover, if the rotation angle range in which the forceps elevator 60 is rotatable, that is, the erecting motion range in which the forceps elevator 60 can be erected and reclined is assumed as an erecting motion range, the angular position θ2 of the forceps elevator 60 when the erecting lever 126 abuts on the wall surface 124$a$ of the lever housing space part 124 is expressed by θ2min as a minimum angular position in the erecting motion range, and the angular position θ2 of the forceps elevator 60 when the erecting lever 126 abuts on the wall surface 124$b$ of the lever housing space part 124 is expressed by θ2max (>θ2min) as a maximum angular position in the erecting motion range.

Figure 9:
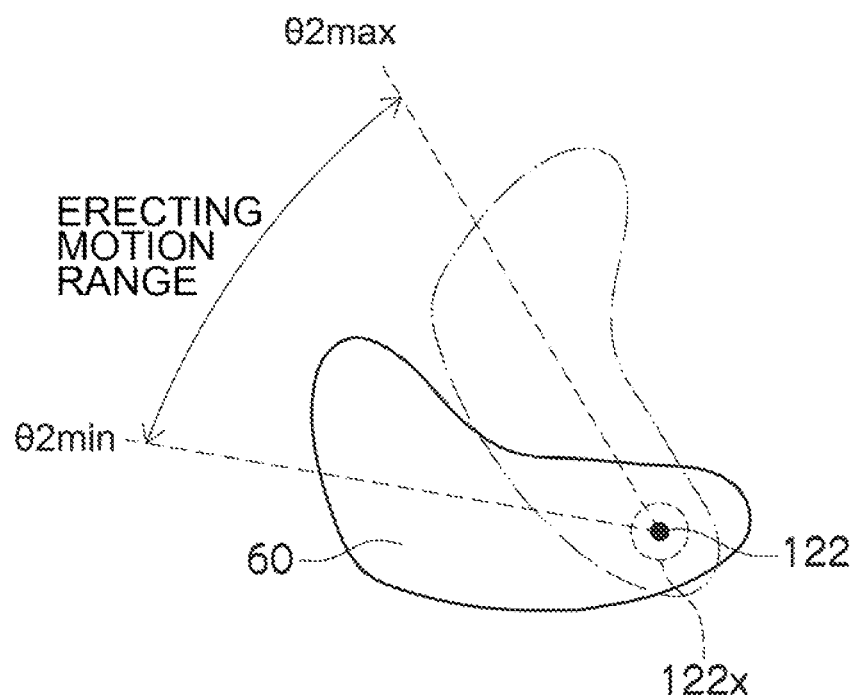
FIG. 9 is a side view illustrating the entire forceps elevator.

At this time, as illustrated in FIG. 9 illustrating the whole of the forceps elevator 60 from the side surface side, when the angular position θ2 is the minimum angular position θ2min, the forceps elevator 60 is in a maximum reclining position in which the forceps elevator 60 is reclined most in the erecting motion range. When the angular position θ2 is the maximum angular position θ2max, the forceps elevator 60 is in a maximum erecting position in which the forceps elevator 60 is erected most in the erecting motion range. The forceps elevator 60 performs the erecting motion within a range from the maximum reclining position to the maximum erecting position.

Moreover, when the operation wire 98 moves forward to the distal end side, since the erecting lever 126 rotates in a direction in which the erecting lever 126 abuts on the wall surface 124$a$ on the distal end side of the lever housing space part 124, the forceps elevator 60 rotates in a reclining direction and the angular position θ2 of the forceps elevator 60 becomes small. When the operation wire 98 moves backward to the proximal end side, since the erecting lever 126 rotates in a direction in which it abuts on the wall surface 124$b$ on the proximal end side of the lever housing space part 124, the forceps elevator 60 rotates in the erecting direction and the angular position θ2 of the forceps elevator 60 becomes large.

Therefore, when the erecting operation lever 74 of the operation part 12 is operated from the proximal end position to the distal end position in the entire operation range to make the angular position θ1 of the erecting operation lever 74 large, the operation wire 98 moves backward to the proximal end side, the forceps elevator 60 of the distal end part 34 performs erecting motion in the erecting direction, and the angular position θ2 of erecting motion becomes large.

Here, the erecting motion range of the forceps elevator 60 may be restricted by any device in the distal end part 34, and it is not limited to the restriction of the motion range of the erecting lever 126 like the present embodiment. For example, it is also possible to adopt a mode in which the erecting motion range of the forceps elevator 60 is directly restricted by a stopper member which abuts on the forceps elevator 60, and so on. Moreover, it is also possible to adopt a mode in which the erecting motion range of the forceps elevator 60 is restricted by restricting the motion range of an arbitrary member which moves in interlock with the forceps elevator 60 in the distal-end-part power transmission mechanism 100 in an arbitrary mode.

Figure 10:
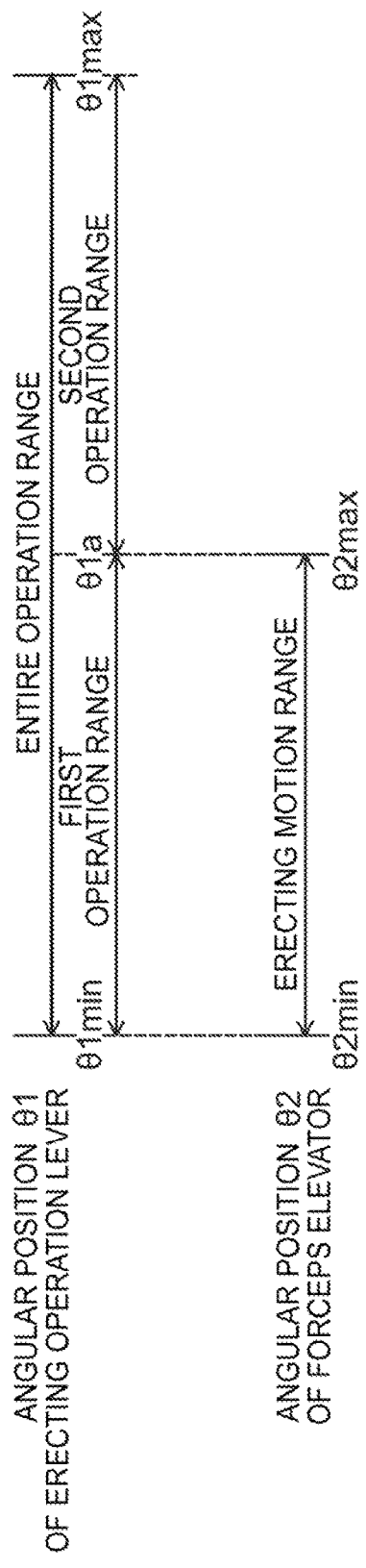
FIG. 10 is a relationship diagram illustrating the relationship between the operation range of an erecting operation lever and the erecting motion range of the forceps elevator in a state where a treatment tool is not led out from a distal end part (treatment tool exit part)

Subsequently, FIG. 10 illustrates a relationship diagram between the operation range of the erecting operation lever 74 and the erecting motion range of the forceps elevator 60 in a state where a treatment tool is not led out from the distal end part 34 (treatment tool exit part 58). The relationship between the operation range of the erecting operation lever 74 and the erecting motion range of the forceps elevator 60 is determined by the size of each of the operation range of the erecting operation lever 74 and the erecting motion range of the forceps elevator 60, the length of the operation wire 98, and so on. In the present embodiment, and these values are set so as to establish the relationship as illustrated in FIG. 10.

As shown in FIG. 10, in a case where the angular position θ1 of the erecting operation lever 74 is the minimum angular position θ1min in the entire operation range, the angular position θ2 of the forceps elevator 60 becomes in the minimum angular position θ2min in the erecting motion range. That is, in a case where the erecting operation lever 74 is in the proximal end position in the entire operation range, the forceps elevator 60 becomes in a maximum reclining position in which the forceps elevator 60 is reclined most.

Then, when the erecting operation lever 74 is operated in a direction where the forceps elevator 60 is erected to make the angular position θ1 of the erecting operation lever 74 gradually larger, the forceps elevator 60 is gradually erected in response to that operation, and the angular position θ2 gradually becomes larger too. However, it may adopt a configuration in which no change is caused in the angular position θ2 of the forceps elevator 60 in a range in which the angular position θ1 of the erecting operation lever 74 changes by a predetermined angle from the minimum angular position θ1min. For example, when a slight play is provided for the erecting lever 126, the angular position θ2 of the forceps elevator 60 substantially becomes the minimum angular position θ2min in an angular position in which the angular position θ1 of the erecting operation lever 74 is larger than θ1min.

Here, in the operation direction (movement direction) of the erecting operation lever 74, it is assumed that a direction to erect the forceps elevator 60 is referred to as the erecting side and a direction to recline the forceps elevator 60 is referred to as the reclining side.

Subsequently, when the angular position θ1 of the erecting operation lever 74 moves to predetermined angular position θ1a which is smaller than the maximum angular position θ1max in the entire operation range, the angular position θ2 of the forceps elevator 60 becomes the maximum angular position θ2max in the erecting motion range.

According to this, in a state where the treatment tool is not led out from the treatment tool exit part 58, the erecting operation lever 74 has the first operation range in which the operation wire 98 is pulled within the erecting motion range of the forceps elevator 60, from the minimum angular position θ1min to the angular position θ1a. Then, when the erecting operation lever 74 is greatly operated toward the erecting side beyond the first operation range, the erecting operation lever 74 has the second operation range in which the operation wire 98 is pulled more, from the angular position θ1a to the maximum angular position θ1max. When the erecting operation lever 74 is operated within the second operation range, the forceps elevator 60 is maintained in the maximum angular position θ2max.

Thus, when the erecting operation lever 74 has the second operation range, even in a case where the bending stiffness of the tool treatment led out from the distal end part 34 through a treatment tool insertion channel is large (in a case where the treatment tool is difficult to bend), it is possible to erect the forceps elevator 60 up to the maximum angular position θ2max by greatly operating the erecting operation lever 74 toward the erecting side beyond the first operation range and operating the erecting operation lever 74 in the second operation range.

Figure 11:
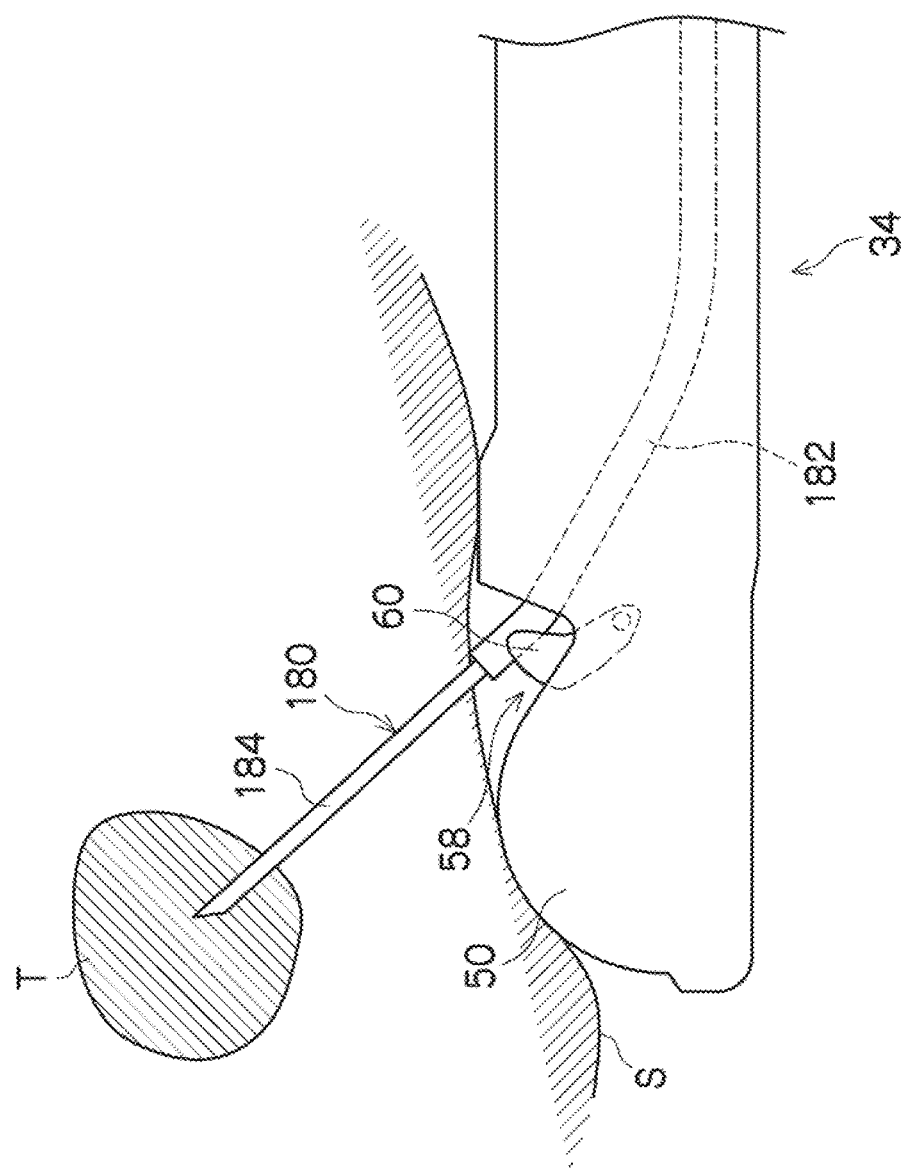
FIG. 11 is a diagram illustrating a state when a puncture needle is led out from a distal end part (treatment tool exit part) and the cellular tissue is collected.

For example, in a case where the cellular tissue is collected from a target site in a subject's body, like FIG. 11, the ultrasonic wave transmitting and receiving surface of the ultrasonic transducer 50 of the distal end part 34 is made to abut on or become close to a wall surface S (body wall) near the target site T, and the position of the target site T is confirmed by an ultrasonic image acquired by the ultrasonic transducer 50. Further, a puncture needle 180 (organization sampling device) as a treatment tool is inserted into the treatment tool insertion channel and led out from the treatment tool exit part 58 of the distal end part 34. Here, for example, the puncture needle 180 is formed with a cylindrical sheath member 182 and a needle tube 184 inserted and disposed in the sheath member 182. When the puncture needle 180 is led out from the treatment tool exit part 58, the needle tube 184 is housed inside the sheath member 182.

Subsequently, the angular position θ2 of the forceps elevator 60 is adjusted by the operation of the erecting operation lever 74, to adjust the lead-out direction (lead-out angle) of the puncture needle 180 from the treatment tool exit part 58 so that the puncture needle 180 is directed in the direction of target site T. Further, the distal end of the needle tube 184 is led out from the sheath member 182 by the operation of the operation part for the puncture needle 180 and the front end the needle tube 184 is inserted from the wall surface S to the target site T. By this means, it is possible to take the cellular tissue of the target site T into the distal end of the needle tube 184. After extracting the puncture needle 180 from the treatment tool insertion channel, it is possible to collect the cellular tissue of the target site T from the needle tube 184.

In such procedure, the puncture needle 180 generally has larger bending stiffness as its outer diameter becomes larger. When the bending stiffness is large, the expansion of the operation wire 98 and the shortening of the wire guide tube 99 are caused. Therefore, as compared with a case where the treatment tool is not led out from the treatment tool exit part 58, sometimes, there may be a case where the angular position θ2 of the forceps elevator 60 becomes small with respect to the angular position θ1 of the erecting operation lever 74. Here, even in a case where the angular position θ2 of the forceps elevator 60 with respect to the angular position θ1 of the erecting operation lever 74 is initially set to an angular position similar to a case where the treatment tool is not led out from the treatment tool exit part 58, there may be a case where the angular position θ2 of the forceps elevator 60 gradually becomes smaller by the restoring force to restore the puncture needle 180 to a straight shape.

In such a case, for example, when the erecting operation lever 74 assumes only the above-mentioned first operation range (see FIG. 10) as the entire operation range, the erecting motion range of the forceps elevator 60 becomes small and cannot be erected up to the original maximum angular position θ2max.

On the other hand, as angular position θ2 of the forceps elevator 60 becomes smaller, that is, as the lead-out angle of the puncture needle 180 becomes smaller, a site which can be punctured by the puncture needle 180 led out from the treatment tool exit part 58 becomes smaller in an observation site imaged in an ultrasonic image, and the site is restricted in a position near the ultrasonic transducer 50. Therefore, when the erecting motion range of the forceps elevator 60 is small, in a case where the target site T is far from the wall surface S and so on, it may be difficult to adjust the position and direction, and so on, of the distal end part 34 such that the target site T is imaged in the ultrasonic image and the puncture needle 180 is directed in a direction of the target site T. Therefore, to facilitate the adjustment of the position and direction of the distal end part 34, it is desirable that the forceps elevator 60 be in a state where it can be erected up to the maximum angular position θ2max.

Especially, in a case where the forceps elevator 60 is erected to be in the maximum angular position θ2max and is used, since the direction of the puncture needle 180 led out from the treatment tool exit part 58 can be specified beforehand, a position through which the puncture needle 180 (needle tube 184) passes on the ultrasonic image can be estimated beforehand without confirming the direction of the puncture needle 180 imaged in the ultrasonic image or the like. Therefore, it is possible to adjust the position and direction and so on of the distal end part 34 such that the target site T is located in the direction of the puncture needle 180, only by confirming the position of the target site T imaged in the ultrasonic image without confirming the direction of the puncture needle 180 imaged in the ultrasonic image or the like. Moreover, the fine control of the angular position θ2 of the forceps elevator 60 can be made unnecessary, and the operation of the forceps elevator 60 can be facilitated. Moreover, the same applies to a case where instruments other than the puncture needle 180 are used as a treatment tool.

In view of this, the erecting operation lever 74 of the present embodiment has: the first operation range in which the operation wire 98 is pulled within the erecting motion range of the forceps elevator 60 in a state where a treatment tool is not led out from the distal end part 34 as illustrated in FIG. 10; and the second operation range in which the operation wire is further pulled when the operation wire is operated more greatly beyond the first operation range.

Figure 12:
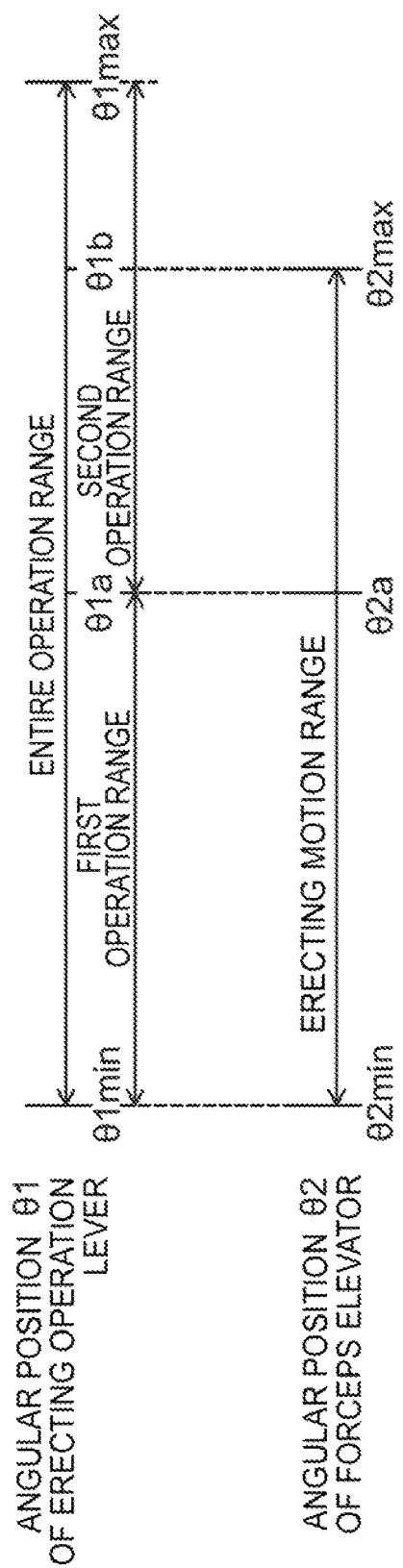
FIG. 12 is a relationship diagram illustrating a relationship between an operation range of the erecting operation lever and an erecting motion range of the forceps elevator in a state where the treatment tool having large bending stiffness is led out from a distal end part (treatment tool exit part)

FIG. 12 illustrates a relationship diagram between the operation range of the erecting operation lever 74 and the erecting motion range of the forceps elevator 60 in a state where a treatment tool having a large bending stiffness is led out from the distal end part 34 (treatment tool exit part 58).

According to this, when the erecting operation lever 74 is operated toward the erecting side to gradually increase the angular position θ1 of the erecting operation lever 74 from the minimum angular position θ1min, the forceps elevator 60 is gradually erected and the lead-out angle of the treatment tool gradually becomes larger together with the angular position θ2 of the forceps elevator 60. However, there is a case where no change is caused in the angular position θ2 of the forceps elevator 60 in a range in which the angular position θ1 of the erecting operation lever 74 changes by a predetermined angle from the minimum angular position θ1min.

Further, when the angular position θ1 of the erecting operation lever 74 becomes the angular position θ1a that is a boundary between the above-mentioned first operation range and the second operation range, the angular position θ2 of the forceps elevator 60 does not become the maximum angular position θ2max in the erecting motion range but becomes the angular position θ2a smaller than the maximum angular position θ2max.

Therefore, in a case where the erecting operation lever 74 can be operated only within the first operation range, the forceps elevator 60 cannot be erected up to the maximum angular position θ2max and its erecting position is restricted up to the angular position θ2a.

Meanwhile, since the erecting operation lever 74 has the second operation range on the erecting side with respect to the first operation range as mentioned above, when the erecting operation lever 74 is further operated toward the erecting side so as to make the angular position θ1 of the erecting operation lever 74 gradually larger from the angular position θ1a, the forceps elevator 60 is further erected and the lead-out angle of the treatment tool gradually becomes larger together with the angular position θ2 of the forceps elevator 60.

Further, when the angular position θ1 of the erecting operation lever 74 becomes a predetermined angular position θ1b equal to or less than the maximum angular positional θ1max, the angular position θ2 of the forceps elevator 60 becomes the maximum angular position θ2max within the erecting motion range.

According to this, in a state where a treatment tool having a large bending stiffness is led out from the treatment tool exit part 58, even when the forceps elevator 60 is not erected up to the maximum angular position θ2max only within the first operation range of the erecting operation lever 74, the forceps elevator 60 can be erected up to the maximum angular position θ2max in the erecting motion range by moving the erecting operation lever 74 to the angular position θ1b in the second operation range which is larger than the first operation range or an angular position larger than the angular position θ1b.

Here, when a case where the use of the second operation range of the erecting operation lever 74 is necessary and a case where it is unnecessary are considered, from the viewpoint of operability, it is preferable that the first operation range of the erecting operation lever 74 be 40% or more and 70% or less with respect to the entire operation range, and it is more preferable that be 50% or more and 70% or less.

Next, a mode when an index is provided, the index for identifying whether the operation range of the erecting operation lever 74 (angular position θ1) is in the minimum angular position θ1min and whether the operation range is the first operation range or the second operation range, is described in the endoscope 1 according to the embodiment illustrated in above-mentioned FIGS. 1 to 12.

Figure 13:
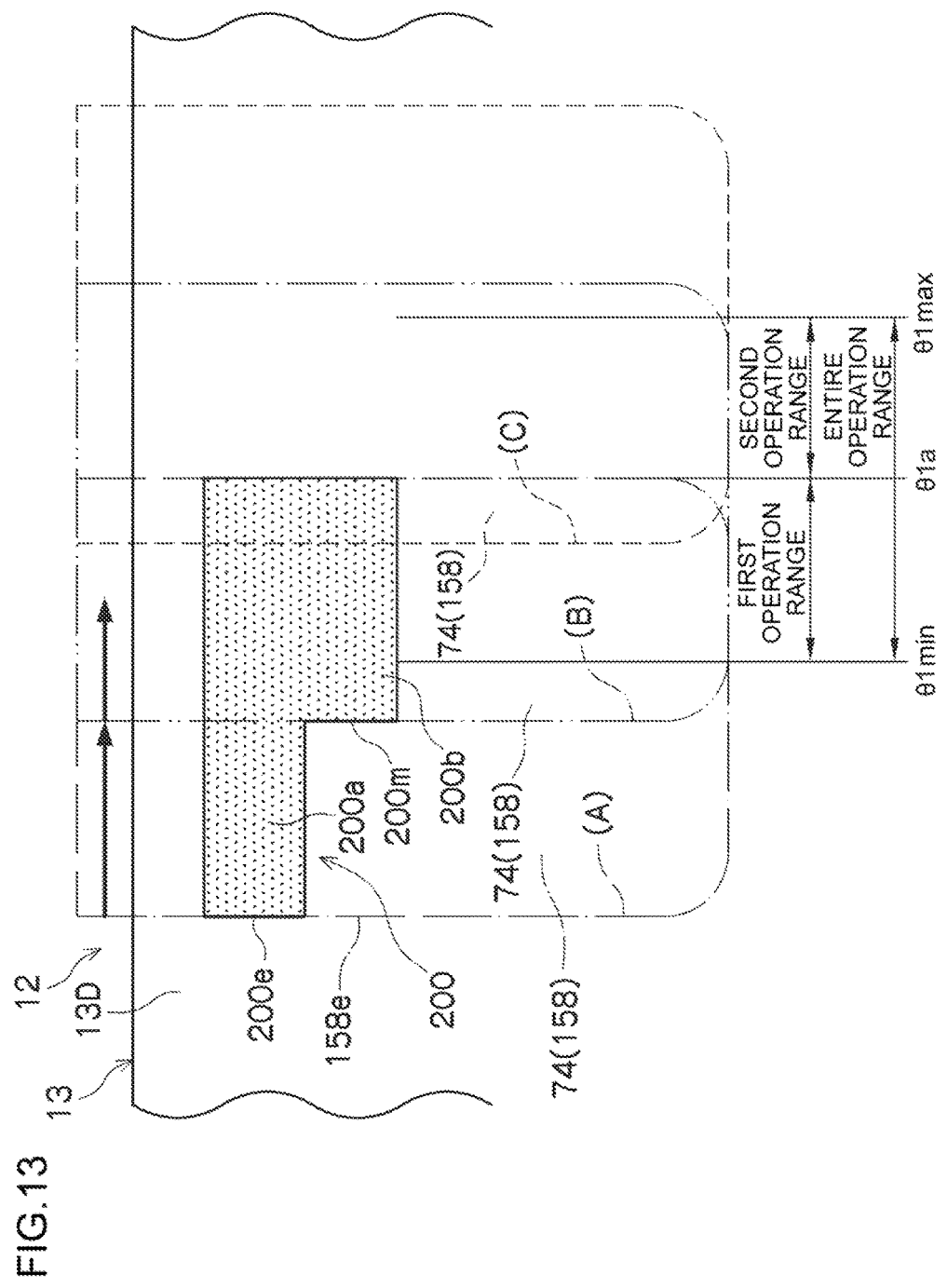
FIG. 13 is an expanded diagram illustrating indices provided in a part which is arranged opposite to the erecting operation lever in the lower surface of the operation part.

FIG. 13 is an expanded diagram illustrating a part which is arranged opposite to the finger hook part 158 of the erecting operation lever 74 in the lower surface 13D of the operation part 12 (casing 13). Here, the finger hook part 158 is expressed by an alternate long and short dash line.

As illustrated in the figure, an index 200 having a color different from that of the lower surface 13D is provided to the lower surface 13D of the operation part 12. For example, the index 200 may be the one which is directly recorded in the lower surface 13D by paint, and so on, or may be a board member fixed to the lower surface 13D. Any device is acceptable as a device which provides the index to the lower surface 13D.

Moreover, the index 200 has a long shape along the direction from the proximal end side to the distal end side of the operation part 12 (back-and-forth direction) which is the movement direction of the erecting operation lever 74, and includes a small width part 200a having a small width on the proximal end side and a large width part 200b having a large width on the distal end side.

This index 200 is provided in a position shielded by the finger hook part 158 of the erecting operation lever 74 in a state where the erecting operation lever 74 is set to the proximal end position (minimum angular position θ1min) in the entire operation range illustrated in Part (A) of the figure. Here, a state where the erecting operation lever 74 is set to the proximal end position corresponds to a state where the forceps elevator 60 is set to the minimum angular position θ2min in the erecting motion range as mentioned above.

Further, a proximal end 200e of the small width part 200a in the index 200 is disposed in a position which substantially matches (substantially matches in the back-and-forth direction) with a proximal end 158e of the finger hook part 158 of the erecting operation lever 74 in the state.

Therefore, when the erecting operation lever 74 is operated toward the erecting side to set to an angular position on the distal end side with respect to the proximal end position, and the forceps elevator 60 is set to a state where it is erected from the minimum angular position θ2min, the small width part 200a in the index 200 is exposed and can be visually checked by an operator.

Moreover, a proximal end 200m of the large width part 200b in the index 200 is disposed in a position which substantially matches (substantially matches in the back-and-forth direction) with the proximal end 158e of the finger hook part 158 in a state where the erecting operation lever 74 is set to the angular position θ1a that is the boundary between the first operation range and the second operation range as illustrated in Part (B) of the figure.

Therefore, when the erecting operation lever 74 is greatly operated toward the erecting side beyond the first operation range and the angular position θ1 of the erecting operation lever 74 is an angular position in the second operation range which is larger than the angular position θ1a, the large width part 200b in the index 200 is exposed and can be visually checked by the operator. Here, the erecting operation lever 74 in Part (C) of the figure shows the one when the angular position θ1 becomes the maximum angular position θ1max.

According to this, whether the angular position θ1 of the erecting operation lever 74 is the minimum angular position θ1min can be known depending on whether the small width part 200a of the index 200 is exposed, that is, whether the small width part 200a is visually checked. And whether the forceps elevator 60 is erected from the minimum angular position θ2min can be known.

By this means, whether the forceps elevator 60 is in a reclined state can be easily known by the operator at the time of insertion and removal of the insertion part 10 into and from the body inside, and it is possible to prevent the insertion and removal operation of the insertion part 10 and the bending operation of the bending part 32 in a state where the forceps elevator 60 is erected. Moreover, since what is required is only to make the index 200 to the operation part 12, it can be simply realized at a low price.

Moreover, the operator can know whether the erecting operation lever 74 moves to the second operation range, based on whether the large width part 200b in the index 200 is exposed, that is, whether the large width part 200b is visually checked. Moreover, it is possible to know whether the forceps elevator 60 is set to the maximum angular position θ2max in a state where a treatment tool is not led out from the distal end part 34 (treatment tool exit part 58) or in a state where a treatment tool of small bending stiffness is led out.

As mentioned above, the index 200 of the embodiment illustrated in FIG. 13 is one example, and other modes are possible as long as it is possible to identify whether the angular position θ1 of the erecting operation lever 74 is the minimum angular position θ1min and whether it is in the first operation range or in the second operation range.

For example, the whole of the index 200 may not be shielded by the erecting operation lever 74 in a state where the erecting operation lever 74 is set to the minimum angular position θ1min, instead, only the distal end side may be exposed. Moreover, the width level relationship between the small width part 200a and the large width part 200b may be reverse. Different modes (colors and patterns, and so on) with the same width or different widths are acceptable.

Figure 14:
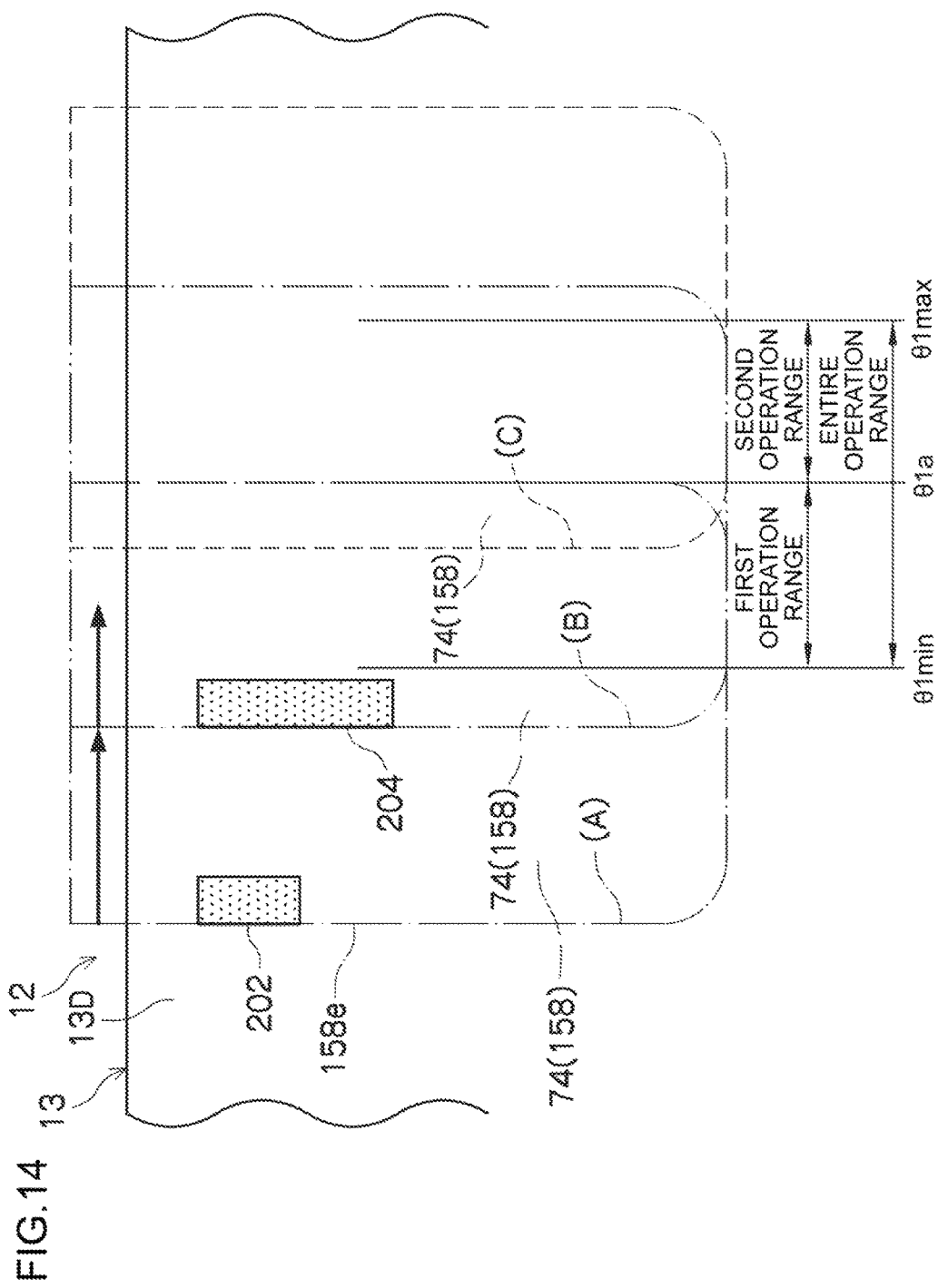
FIG. 14 is a diagram illustrating another mode of indices.

Moreover, as illustrated in FIG. 14, the index may include an index 202 and an index 204 which are configured by leaving only the proximal end part of the small width part 200a and the proximal end part of the large width part 200b in the index 200 in FIG. 13. The index 202 and the index 204 may have the same width.

Moreover, it may be designed such that the index can identify only any one of whether angular position θ1 of the erecting operation lever 74 is the minimum angular position θ1min and whether it is in the first operation range or in the second operation range. The index 200 in FIG. 13 may be formed with only any one of the small width part 200a and the large width part 200b. Moreover, the index in FIG. 14 may include only any one of the index 202 and the index 204.

In addition, even in a case where the erecting operation lever 74 does not have the second operation range and has only the first operation range, it is effective to provide with an index which shows whether the angular position θ1 of the erecting operation lever 74 is the minimum angular position θ1min, in the same way as the above-mentioned embodiment.

Next, a mode is described where a locking mechanism (load generating device) which locks the movement (rotation) of the erecting operation lever 74 when the erecting operation lever 74 is operated in the second operation range, in the endoscope 1 of the embodiment illustrated in above-mentioned FIG. 1 to 12 or in the endoscope 1 of the embodiments which have the indices illustrated in above-mentioned FIGS. 13 and 14.

Figure 15:
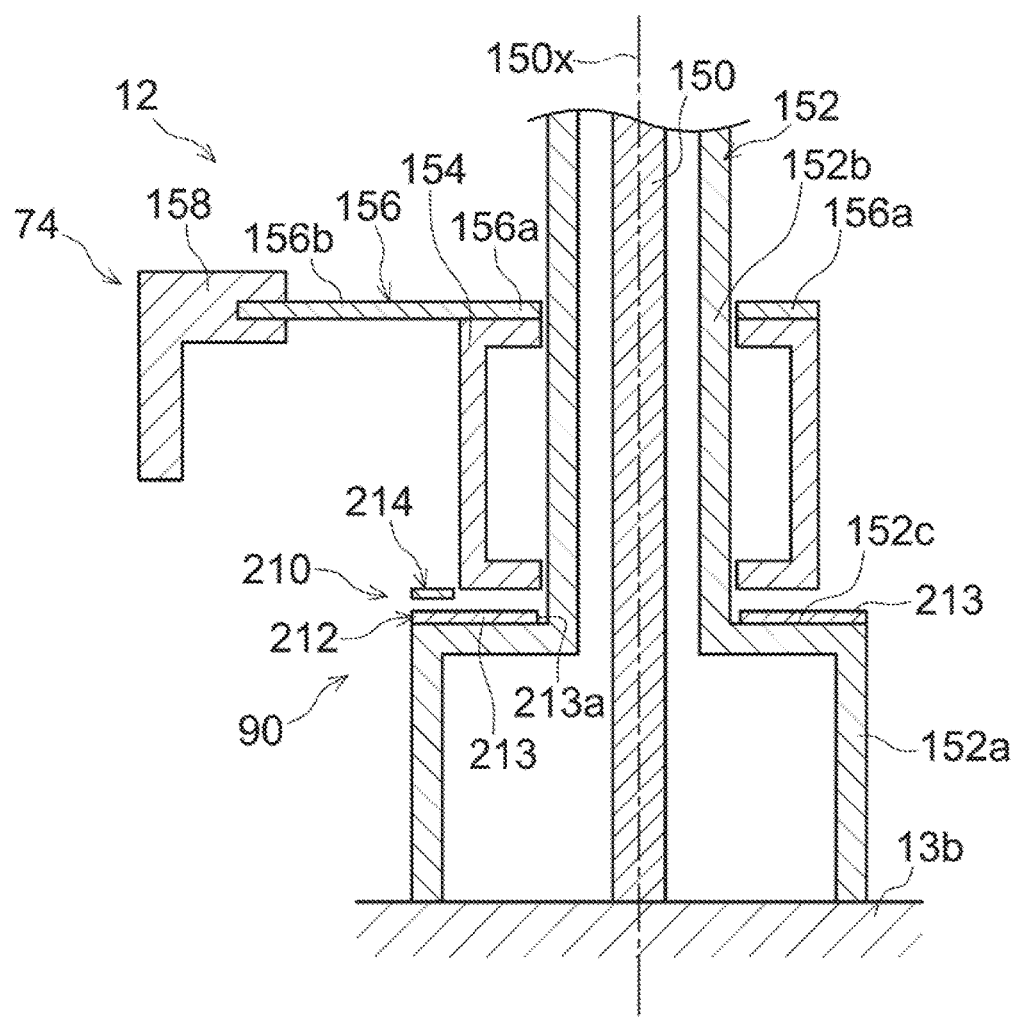
FIG. 15 is a diagram illustrating a locking mechanism provided in a transmission mechanism in the operation part.
Figure 16:
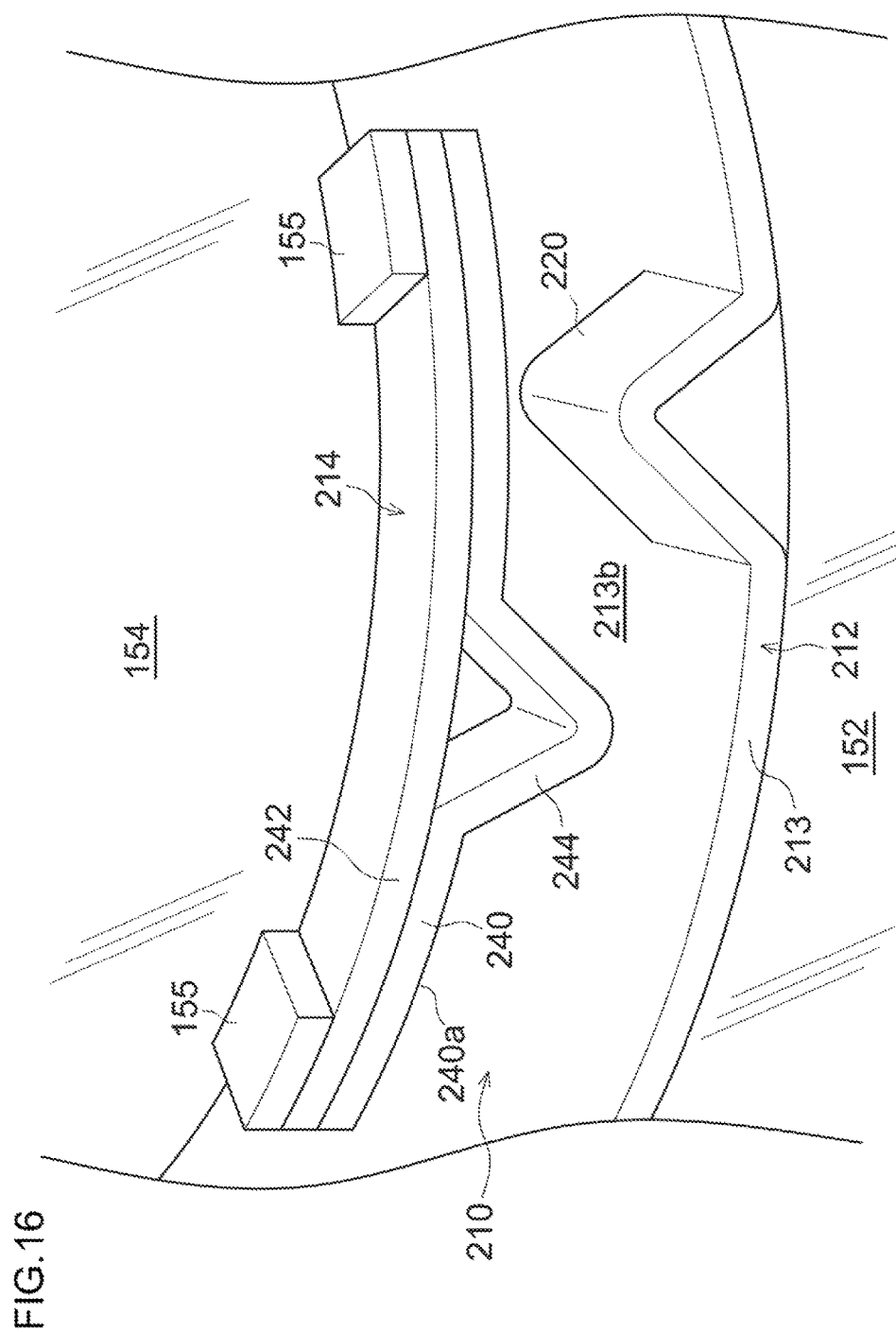
FIG. 16 is an expanded perspective view illustrating the locking mechanism provided in the transmission mechanism in an operation part.

FIG. 15 is a diagram illustrating the erecting operation lever 74, the coupling member 156, the rotating drum 154 and the fixing shaft 152 in the operation-part power transmission mechanism 90 in FIG. 7, and FIG. 16 is an expanded perspective view illustrating the locking mechanism provided in the operation-part power transmission mechanism 90.

As illustrated in these figures, there provided is the locking mechanism 210 which locks the movement of the erecting operation lever 74 when the erecting operation lever 74 is operated in the second operation range, between the rotating drum 154 which rotates around the axis 150x together with the rotation operation of the erecting operation lever 74 and the fixing shaft 152 fixed to the casing 13 by the support part 13b.

The locking mechanism 210 includes: a fixed part 212 which is provided in the operation part 12 (casing 13) by being fixed to the fixing shaft 152; and a movable part 214 which is provided integrally with the erecting operation lever 74 by being fixed to the rotating drum 154 and moves relative to the fixed part 212.

The fixed part 212 includes a disc-shaped tubular member 213 having a through hole 213a in a central part thereof. The small diameter part 152b of the fixing shaft 152 is inserted into the through hole 213a and the fixed part 212 is fixed to a stepped part 152c that is a coupling part between the large diameter part 152a and the small diameter part 152b of the fixing shaft 152 by a screw and so on. Here, the central axis of the fixed part 212 is disposed on the same axis as the axis 150x.

Moreover, the fixed part 212 is provided with a locking pin 220 that projects from a flat plate surface 213b toward the side of the movable part 214, in an outer peripheral part as illustrated in FIG. 16. The locking pin 220 has a chevron shape along the circumferential direction around the axis 150x.

Meanwhile, the movable part 214 is formed by overlapping two long and thin tubular members 240 and 242 which can be elastically deformed as illustrated in FIG. 16, and both end parts of those tubular members 240 and 242 are fixed to two convex parts 155 which project in the radial direction from the end part on the proximal end side of the rotating drum 154 by a screw and so on. Further, the movable part 214 including those tubular members 240 and 242 is disposed in a position facing the outer peripheral part of the fixed part 212.

Moreover, in the tubular member 240 disposed on the side of the fixed part 212 among the tubular members 240 and 242, a locking projection 244 that projects on the side of the fixed part 212 from a flat plate surface 240a is provided. The locking projection 244 has a chevron shape in the circumferential direction around the axis 150x.

By this means, the tubular members 240 and 242 support the locking projection 244 as an elastic support member which is elastically deformable. Here, the movable part 214 may be composed of only one tubular member 240. In the following, explanation is given assuming that the movable part 214 is composed of only one tubular member 240.

The locking pin 220 of the fixed part 212 and the locking projection 244 of the movable part 214, which are formed in this way, are disposed in positions that intersect with a cylindrical surface having the same diameter with respect to the axis 150x. The fixed part 212 and the movable part 214 are disposed with a distance in-between such that the locking pin 220 and the locking projection 244 are brought into contact with each other when the movable part 214 rotates around the axis 150x together with the rotating drum 154 by the rotation operation of the erecting operation lever 74.

Figure 17:
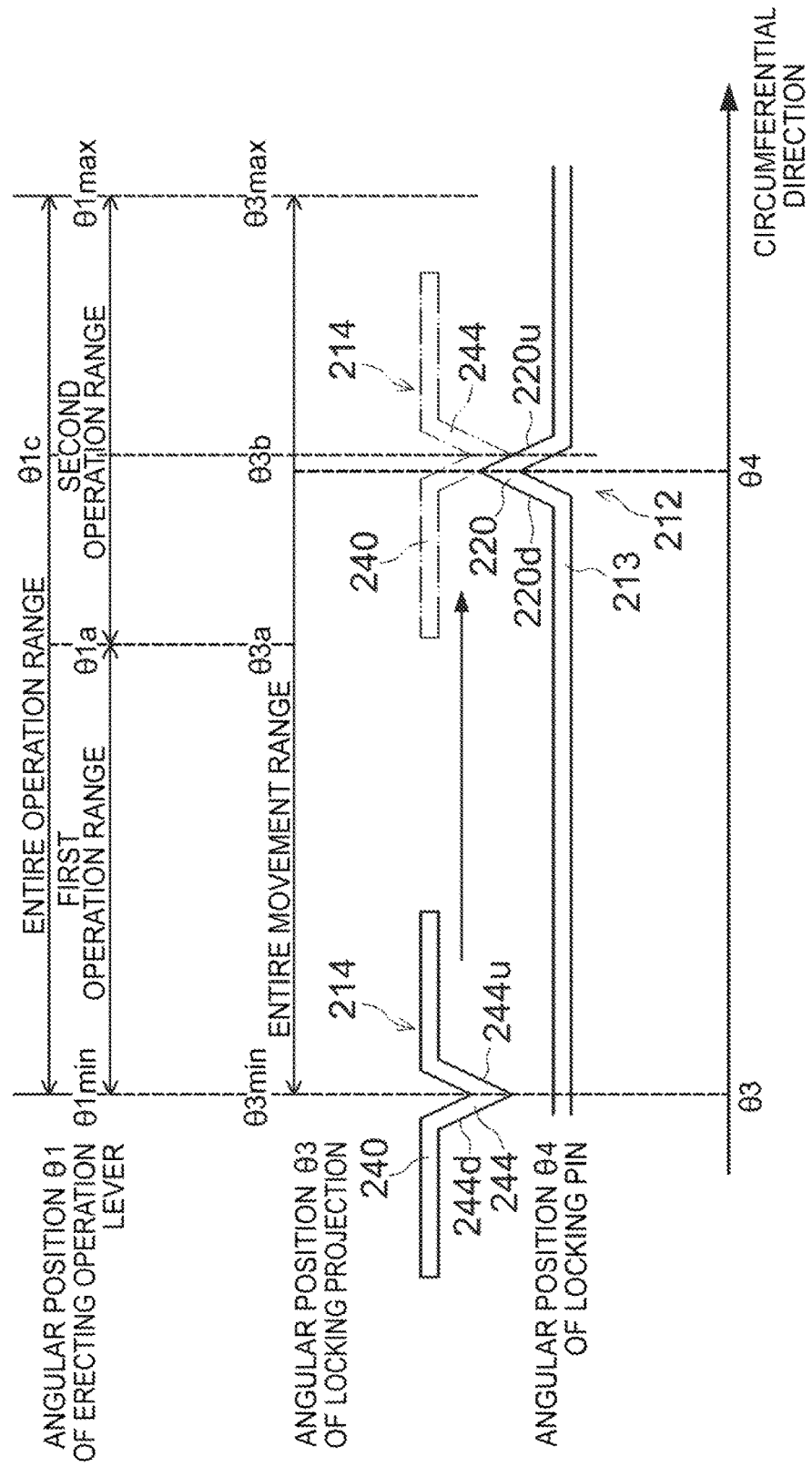
FIG. 17 is a diagram simply illustrating configurations of a fixed part and movable part of the locking mechanism along the circumferential direction when they are developed in a plane, and is a diagram illustrating a relationship with an angular position of the erecting operation lever.

FIG. 17 is a diagram simply illustrating configurations of the fixed part 212 and the movable part 214 along the circumferential direction (a direction around the axis 150x) when they are exploded in a plane, and is a diagram illustrating a relationship with the angular position θ1 of the erecting operation lever 74.

First, the position of the locking projection 244 when the locking projection 244 of the movable part 214 (the center of the locking projection 244) is set to the position of rotation angle θ3 around the axis 150x is expressed as angular position θ3, and the position of the locking pin 220 when the locking pin 220 of the fixed part 212 (the center of the locking pin 220) is arranged in the position of rotation angle θ4 around the axis 150x is expressed as angular position θ4. Moreover, assuming that the rotation angle range in which the locking projection 244 is rotatable, that is, the movement range in which the locking projection 244 is movable is referred to as the entire movement range, the angular position θ3 of the locking projection 244 when the angular position θ1 of the erecting operation lever 74 is set to the minimum angular position θ1min in the entire operation range is expressed by θ3min as the minimum angular position in the entire movement range, and the angular position θ3 of the locking projection 244 when the angular position θ1 of the erecting operation lever 74 is set to the maximum angular position θ1max in the entire operation range is expressed by θ3max (>θ3min) as the maximum angular position in the entire movement range.

At this time, the angular position θ3 of the locking projection 244 becomes the minimum angular position θ3min in the entire movement range when the angular position θ1 of the erecting operation lever 74 is the minimum angular position θ1min as illustrated in the figure. Moreover, the angular position θ1 of the erecting operation lever 74 becomes the maximum angular position θ3max in the entire movement range when the angular position θ1 of the erecting operation lever 74 is the maximum angular position θ1max.

Further, the locking projection 244 moves in a range from the minimum angular position θ3min to the maximum angular position θ3max in response to the movement of the erecting operation lever 74 in a range from the minimum angular position θ1min to the maximum angular position θ1max.

Meanwhile, the locking pin 220 is, at least, arranged within the range of the angular position θ3 of the locking projection 244 when the angular position θ1 of the erecting operation lever 74 is set to the second operation range. That is, if the angular position θ3 of the locking projection 244 is assumed as θ3a when the erecting operation lever 74 is in the angular position θ1a that is the boundary between the first operation range and the second operation range, the locking pin 220 is arranged in a position where the angular position θ4 corresponds to the angular position θ3b which is, at least, the angular position θ3a or more and the angular position θ3max or less.

Here, the figure does not mean that the locking projection 244 is set in a position of the same rotation angle in the direction around the axis 150x as the erecting operation lever 74. The relative positional relationship between the locking projection 244 and the erecting operation lever 74 is not limited to the specific one.

According to such arrangement of the locking projection 244 and the locking pin 220, when the erecting operation lever 74 is operated from the minimum angular position θ1min toward the erecting side to make the angular position θ1 of the erecting operation lever 74 larger, the locking projection 244 also moves toward the erecting side and the angular position θ3 of the locking projection 244 gradually becomes larger from the minimum angular position θ3min. Here, the erecting side related to the locking projection 244 denotes a direction to erect the forceps elevator 60 in the movement direction of the movable part 214 (locking projection 244) relative to the fixed part 212 (locking pin 220), and the reclining side denotes a direction to recline the forceps elevator 60.

Further, when the erecting operation lever 74 moves to the second operation range and the locking projection 244 moves to the angular position θ3b, a slope surface 224u on the erecting side of the locking projection 244 abuts on, a slope surface 220d on the reclining side of the locking pin 220 and they are engaged with each other. By this means, the locking projection 244 and the locking pin 220 are engaged with each other on the reclining side, and a load is applied to the movement of the locking projection 244 toward the erecting side so that the movement of the erecting operation lever 74 toward the erecting side is locked.

Here, the engagement between the locking projection 244 and the locking pin 220 on the reclining side means an engagement when a slope surface 244u on the erecting side of the locking projection 244 abuts on the slope surface 220d on the reclining side of the locking pin 220, that is, when the locking projection 244 is on the reclining side relative to the locking pin 220. On the contrary, the engagement on the erecting side means an engagement when a slope surface 244d on the reclining side of the locking projection 244 abuts on a slope surface 220u on the erecting side of the locking pin 220, that is, when the locking projection 244 is on the erecting side relative to the locking pin 220.

Here, when an amount of force equal to or greater than a certain level is applied to the locking projection 244 (movable part 214) toward the erecting side to release the engagement by an operator's operation of the erecting operation lever 74, the tubular member 240 that supports the locking projection 244 is elastically deformed and the locking projection 244 rides across the locking pin 220. By this means, the engagement between the locking projection 244 and the locking pin 220 on the reclining side is released.

Moreover, in the following, the description that engagement is released means that: the locking projection 244 rides across the locking pin 220 by the movement of the locking projection 244 toward the erecting side in the case of engagement on the reclining side; and the locking projection 244 rides across the locking pin 220 by the movement of the locking projection 244 toward the reclining side in the case of engagement on the erecting side.

After the engagement between the locking projection 244 and the locking pin 220 on the reclining side is released, when the erecting operation lever 74 is further operated toward the erecting side and the locking projection 244 moves toward the erecting side, the angular position θ3 of the locking projection 244 becomes larger from angular position θ3b. Then, when the erecting operation lever 74 becomes the maximum angular position θ1max, the angular position θ3 of the locking projection 244 becomes the angular position θ3max.

Meanwhile, after engagement between the locking projection 244 and the locking pin 220 on the reclining side is released, in the angular position θ1c (see FIG. 17) of the erecting operation lever 74 when the slope surface 244d on the reclining side of the locking projection 244 abuts on the slope surface 220u on the erecting side of the locking pin 220, the locking projection 244 and the locking pin 220 are engaged with each other on the erecting side and a load is applied to the movement of the locking projection 244 toward the reclining side. Thus, the movement of the erecting operation lever 74 toward the reclining side is locked.

Here, in a case where the locking projection 244 and the locking pin 220 are engaged with each other on the erecting side and in a case where they are engaged on the reclining side, the angular position θ3 of the locking projection 244 and the angular positions θ1 of the erecting operation lever 74 are exactly different between those cases. However, since the difference is small, in the following, when the locking projection 244 and the locking pin 220 are engaged with each other, even in either of engagement on the erecting side or on the reclining side, the angular position of the locking projection 244 at the time of engagement is assumed as the angular position of the locking pin 220, and the angular position of the erecting operation lever 74 at the time of engagement is assumed as the angular position of the erecting operation lever 74 corresponding to the angular position of the locking projection 244 at the time of the engagement.

In a case where the locking projection 244 and the locking pin 220 are engaged with each other on the erecting side, when an amount of force equal to or greater than a certain level is applied to the locking projection 244 (movable part 214) toward the reclining side to release the engagement by an operator's operation of the erecting operation lever 74, that is, when a force having an amount equal to or greater than an required amount to release the engagement between the locking projection 244 and the locking pin 220 on the erecting side is applied to the movement of the locking projection 244 toward the reclining side, the engagement between the locking projection 244 and the locking pin 220 on the erecting side is released in the same way as the above-mentioned case. Then, when the erecting operation lever 74 is further operated toward the reclining side, the locking projection 244 moves toward the reclining side together with the erecting operation lever 74. When the erecting operation lever 74 reaches the minimum angular position θ1min, the angular position θ3 of the locking projection 244 becomes the minimum angular position θ3min.

By the way, in a case where a treatment tool is led out from the distal end part 34 (treatment tool exit part 58), the restoring force to restore the treatment tool to a straight shape is applied to the forceps elevator 60, and the force toward the reclining side is applied to the movable part 214 through the operation wire 98, the slider 96 and the rotating drum 154. Meanwhile, the system is configured such that the engagement between the locking projection 244 and the locking pin 220 on the erecting side cannot be easily released by the amount of force applied from the treatment tool in such a way.

Therefore, when the erecting operation lever 74 is operated toward the erecting side and, in the second operation range, the locking projection 244 is moved toward the erecting side beyond the angular position θ3b in which the locking projection 244 and the locking pin 220 are engaged with each other, even if an operator releases fingers from the erecting operation lever 74 or does not hold the position of the erecting operation lever 74 by large holding force, it is possible to lock the erecting operation lever 74 in a position when the locking projection 244 and the locking pin 220 are engaged on the erecting side, and the angular position of the forceps elevator 60 and the lead-out angle of the treatment tool can be maintained.

Especially, as illustrated in FIGS. 32 and 33, when the erecting operation lever 74 is operated by the thumb of the left hand and the forceps elevator 60 is erected up to the maximum angular position θ2max in a case where the bending stiffness of the treatment tool is large, it is necessary to greatly bend the joint of the thumb so as to operate the erecting operation lever 74 to the second operation range as illustrated in FIG. 33. Further, in a case where the locking mechanism 210 does not exist, since it is necessary to keep applying the force toward the erecting side to the erecting operation lever 74 against the restoring force to restore the treatment tool to a straight shape, it burdens on the finger. However, by engaging the locking projection 244 and the locking pin 220 with each other on the erecting side using the locking mechanism 210 of the present embodiment, the operator can release the thumb from the erecting operation lever 74 or does not have to keep applying a large force to the erecting operation lever 74 and an operation load is mitigated.

Subsequently, a setup position of the locking pin 220 of the fixed part 212 is described. FIG. 17 shows that the setup position of the locking pin 220 may be an arbitrary angular position θ3b that falls within an angular position range in which the locking projection 244 of the movable part 214 moves when the erecting operation lever 74 is operated in the second operation range, that is, within the range from the angular position θ3a to the angular position θ3max. Although the setup position is not limited to a specific position, it may be arranged in a characteristic angular position as follows.

Figure 18:
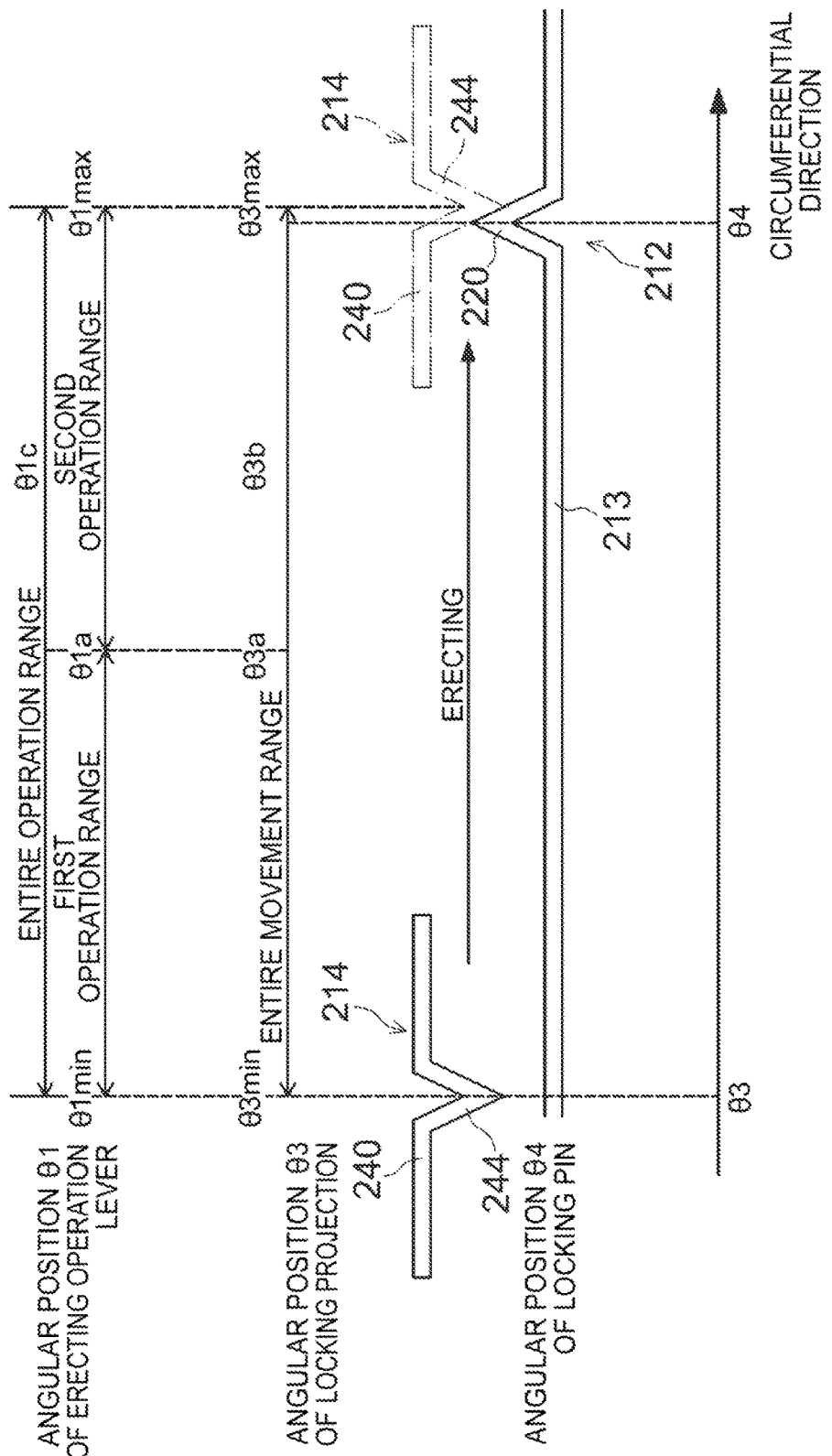
FIG. 18 is a diagram illustrating a specific example about a position of a locking pin, and is a diagram simply illustrating configurations of a fixed part and movable part of a locking mechanism along the circumferential direction when they are developed in a plane.

FIG. 18 is a diagram illustrating configurations of the fixed part 212 and the movable part 214 along the circumferential direction together with a relationship with the angular position θ1 of the erecting operation lever 74 in the same way as FIG. 17. The locking pin 220 in the figure is arranged in an angular position which substantially matches the maximum angular position θ3max of the locking projection 244. According to this, the locking projection 244 and the locking pin 22 are engaged with each other on the erecting side when the erecting operation lever 74 is operated to reach the maximum angular position θ1max. Therefore, the movement of the erecting operation lever 74 toward the reclining side can be locked in the maximum angular position θ1max.

Thus, by locking the erecting operation lever 74 in maximum angular position θ1max, the forceps elevator 60 can be held in maximum angular position θ2max (maximum erecting position) regardless of the degree of the bending stiffness of the treatment tool, except a case where the treatment tool led out from the distal end part 34 is unexpected.

Figure 19:
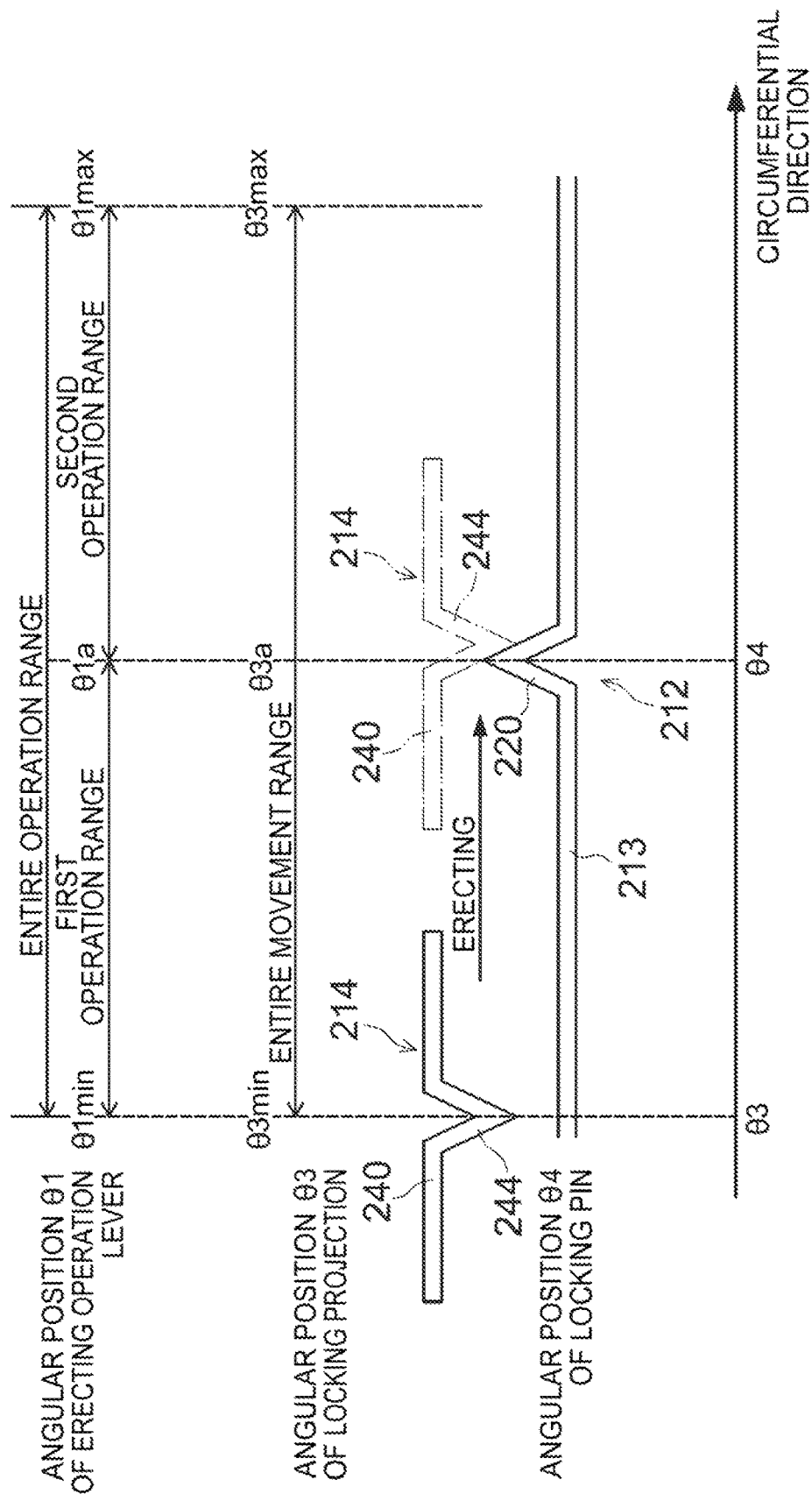
FIG. 19 is a diagram illustrating a specific example about the position of a locking pin, and is a diagram simply illustrating configurations of the fixed part and the movable part of the locking mechanism along the circumferential direction when they are developed in a plane.

FIG. 19 is a diagram illustrating configurations of the fixed part 212 and the movable part 214 along the circumferential direction together with the relationship with the angular position θ1 of the erecting operation lever 74 in the same way as FIG. 17.

The locking pin 220 in the figure is arranged in an angular position which substantially matches the angular position θ3a of the locking projection 244. The angular position θ3a of the locking projection 244 is an angular position of the locking projection 244 when the erecting operation lever 74 is in the angular position θ1a that is the boundary between the first operation range and the second operation range as mentioned above.

According to this, the locking projection 244 and the locking pin 22 are engaged with each other on the erecting side when the erecting operation lever 74 is operated to reach the angular position θ1a that is the boundary between the first operation range and the second operation range.

Therefore, the movement of the erecting operation lever 74 toward the reclining side can be locked in the angular position θ1a.

Thus, by locking the erecting operation lever 74 in maximum angular position θ1a, if the degree of the bending stiffness of the treatment tool led out from the distal end part 34 is normal, the forceps elevator 60 can be held in the maximum angular position θ2max (maximum erecting position).

Moreover, the locking projection 244 and the locking pin 220 are engaged with each other on the reclining side before they are engaged on the erecting side, and, when an operator operates the erecting operation lever 74 to apply an amount of force equal to or greater than a certain level toward the erecting side to the locking projection 244, the engagement on the reclining side is released and they are engaged on the erecting side. Therefore, the operator can know that the operation of the erecting operation lever 74 shifts from the first operation range to the second the operation range, from a rapid change in the amount of force required for the operation of the erecting operation lever 74 toward the erecting side.

As mentioned above, the fixed part 212 and the movable part 214 of the locking mechanism 210 only have to include the locking pin 220 and the locking projection 244 which are mutually engaged parts, or only have to include an elastic support member which supports the locking projection 244 in addition to them. Other parts can be changed to have an arbitrary configuration. For example, the locking pin 220 may be formed not to be the disc-shaped tubular member 213. The locking pin 220 may be formed to be a tubular member having a size corresponding to only the periphery in a position where the locking pin 220 is arranged, and the tubular member may be fixed to the stepped part 152c of the fixing shaft 152. Moreover, the fixed part 212 may be fixed to an arbitrary material fixed to the casing 13 of the operation part 12 instead of the stepped part 152c of the fixing shaft 152, and the movable part 214 may be fixed to an arbitrary position of the rotating drum 154 or an arbitrary part of an arbitrary member coupled with the erecting operation lever 74 instead of the convex part 155 which projects in the radial direction from the end part on the proximal end side of the rotating drum 154. Moreover, the elastic support member which supports the locking projection 244 of the movable part 214 may be the one which supports the locking projection 244 by an arbitrary elastic member such as a spring, instead of the tubular members 240 and 242 whose both ends are fixed such that their central parts are elastically deformable as mentioned above. And, the elastic support member may be the one whole of which faces a plane and is fixed to a member such as the rotating drum 154.

In addition, as a mode of the locking mechanism 210, a mode in which the fixed part 212 and the movable part 214 mutually adopt configurations of the other is acceptable. That is, regarding the locking mechanism 210 including the fixed part 212 and the movable part 214 of arbitrary configurations, it is possible to adopt a mode of the locking mechanism in which the configuration of the fixed part 212 is used as a configuration of a movable part and the configuration of the movable part 214 is used as a configuration of a fixed part.

These modifiable matters related to the fixed part 212 and the movable part 214 of the locking mechanism 210 are applicable also in the embodiments shown below.

Next, modified examples of the above-mentioned locking mechanism 210 and its peripheral parts are described. In the following explanation, parts in which a modification is made to the above-mentioned embodiment are mainly described, and the same reference numerals as the above-mentioned embodiment are assigned to components of parts configured in the same way as the above-mentioned embodiment, and the explanation is omitted. Moreover, the modified examples described below can be arbitrarily combined and adopted.

First, a modified example of the movable part 214 of the locking mechanism 210 is described.

In the locking mechanism 210 illustrated in FIGS. 15 to 19, the movement of the erecting operation lever 74 is locked by the engagement between the convex parts of the locking pin 220 of the fixed part 212 and the locking projection 244 of the movable part 214. However, the movement of the erecting operation lever 74 may be locked by engagement by friction using a friction plate as the movable part 214.

Figure 20:
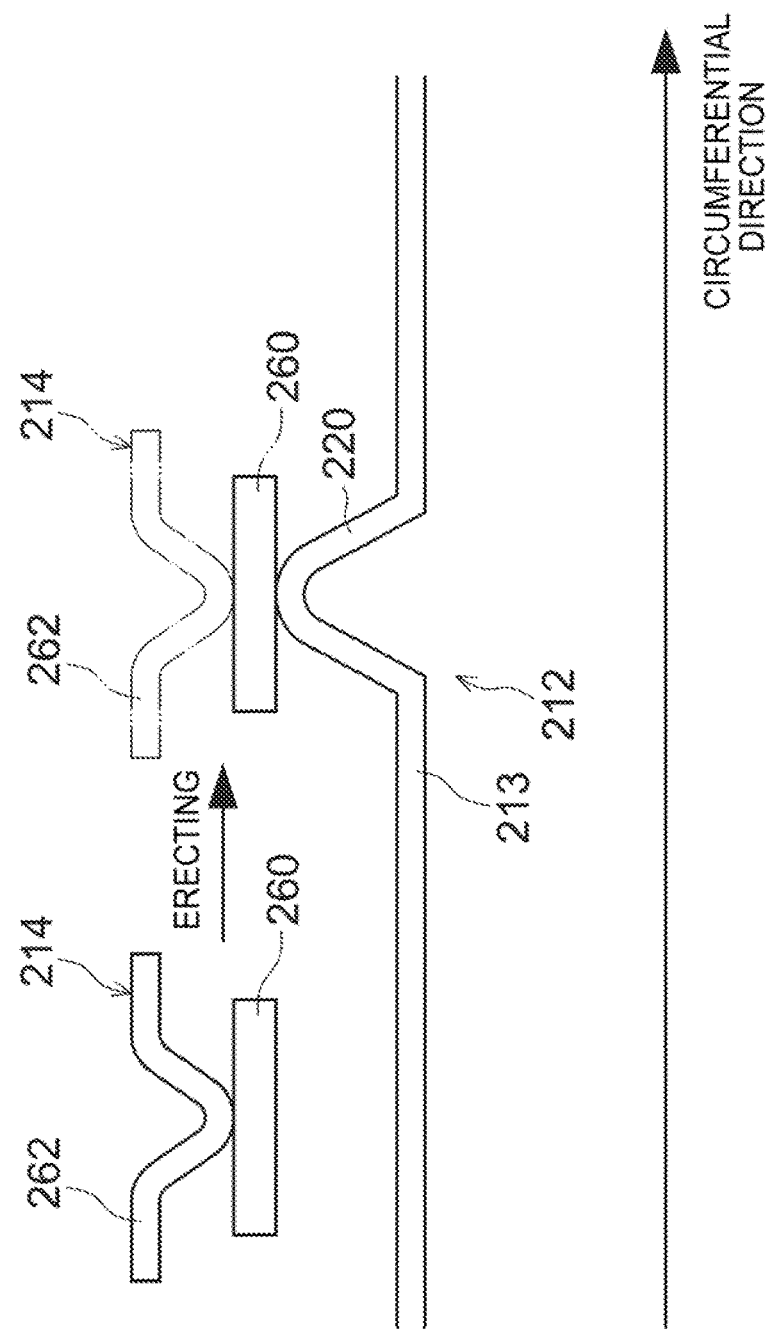
FIG. 20 is a diagram illustrating a modified example of the movable part of the locking mechanism.

FIG. 20 is a diagram illustrating a configuration of the locking mechanism 210 along the circumferential direction in that case. As illustrated in the figure, the movable part 214 includes: a friction plate 260; and a plate spring 262 which supports the friction plate 260. According to this, when the erecting operation lever 74 is operated in the second operation range, the locking pin 220 of the fixed part 212 slidingly contacts (is engaged) with the friction plate 260 as a sliding contact member and is brought into pressure contact (pressingly contacts) with the friction plate 260 by the plate spring 262 to generate the friction force. Thus, the movement of the erecting operation lever 74 is locked. Here, an arbitrary-shaped sliding contact member which slidingly contacts with the friction plate 260 and generates the friction force can be used instead of the locking pin 220 in this mode.

Next, a modified example of the fixed part 212 of the locking mechanism 210 is described.

The fixed part 212 of the locking mechanism 210 illustrated in FIGS. 15 to 19 has a configuration including one locking pin 220. However, as a configuration including multiple locking pins, the locking mechanism 21 may be configured to lock the movement of the erecting operation lever 74 in multiple positions when the erecting operation lever 74 is operated in the second operation range.

Figure 21:
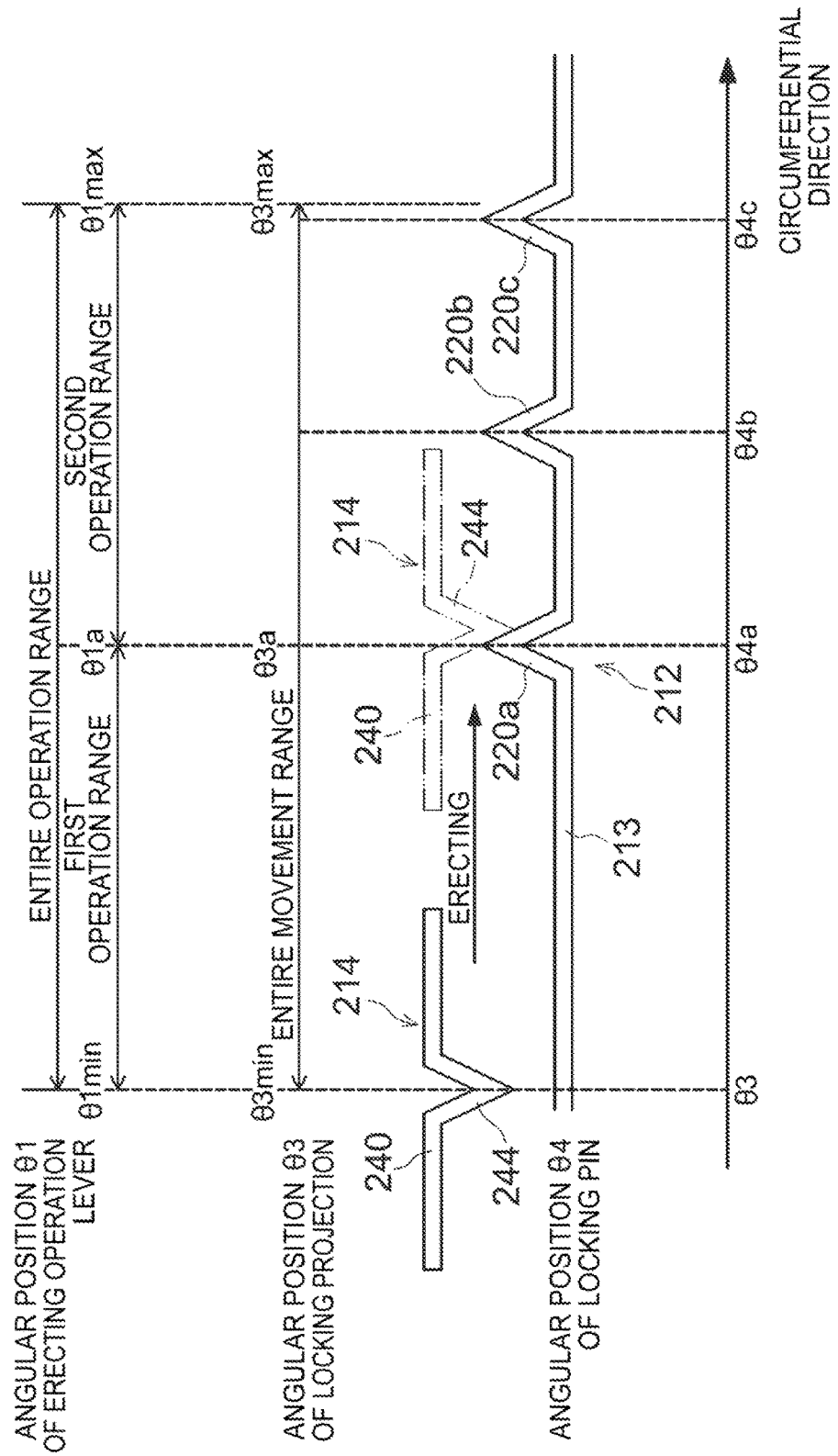
FIG. 21 is a diagram illustrating a modified example of the fixed part of the locking mechanism, and is a diagram where multiple locking pins are discretely disposed.

FIG. 21 is a diagram illustrating a configuration of the locking mechanism 210 in the circumferential direction in such the case, in the same way as FIG. 17. As illustrated in the figure, the fixed part 212 includes three locking pins 220a, 220b and 220c respectively disposed in different angular positions θ4a, θ4b and θ4c along the movement direction of the movable part 214. In this configuration, when the erecting operation lever 74 is operated in the second operation range, if the locking projection 244 of the movable part 214 moves to any one of the positions of the angular positions θ4a, θ4b and θ4c, the locking projection 244 is engaged with any one of the locking pins 220a, 220b or 220c. Accordingly, the movement of the erecting operation lever 74 is locked in three positions in the second operation range. Here, the number of locking pins included in the fixed part 212 may not be three but may be two, four or more, and the angular positions in which multiple locking pins are placed may be equal intervals or may not be at equal intervals.

Figure 22:
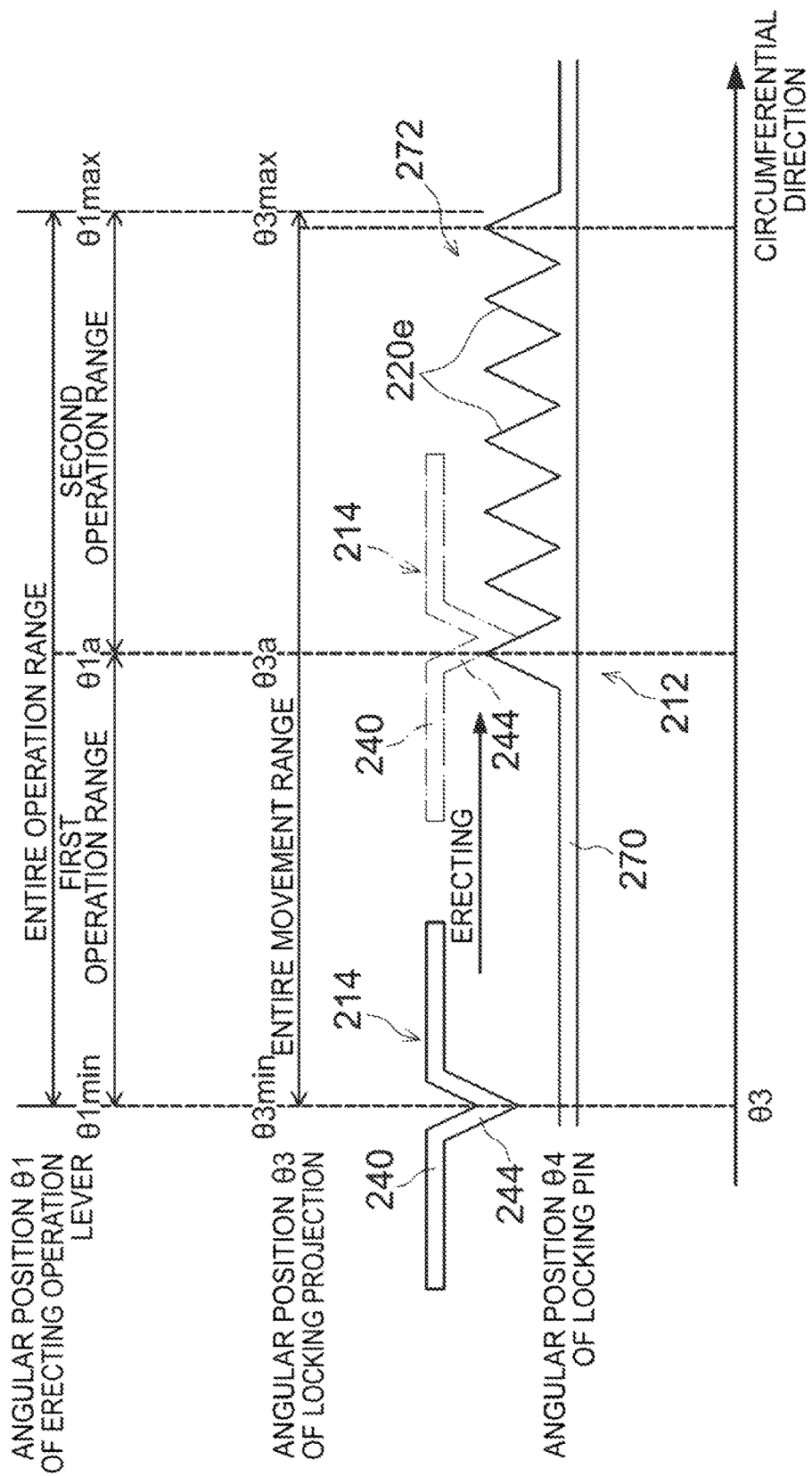
FIG. 22 is a diagram illustrating a modified example of a fixed part of the locking mechanism, and is a diagram where multiple locking pins are continuously disposed.
Figure 23:
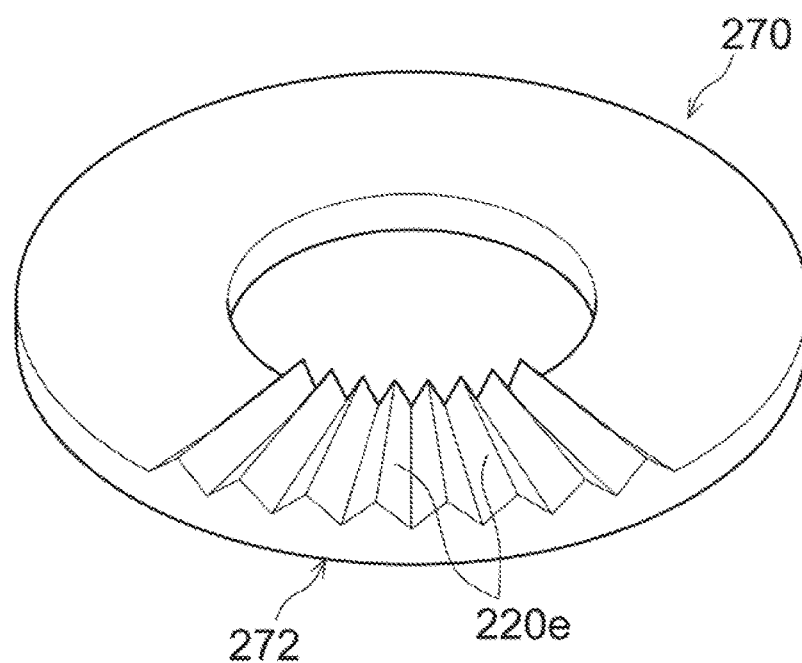
FIG. 23 is a perspective view of a latch board forming a locking pin in FIG. 22.

Moreover, multiple locking pins in the fixed part 212 may not be discretely disposed like the mode in FIG. 21, but locking pins 220e may be continuously disposed as illustrated in FIG. 22. In that case, those locking pins 220e correspond to latch teeth 272 and can be formed with a latch board 270 as illustrated in FIG. 23. By this means, it is possible to lock the movement of the erecting operation lever 74 in continuous positions in the second operation range of the erecting operation lever 74. Here, the latch teeth 272 may be disposed in a range (from angular position θ3a to angular position θ3max) corresponding to the whole of the second operation range or may be disposed in a partial range.

Figure 24:
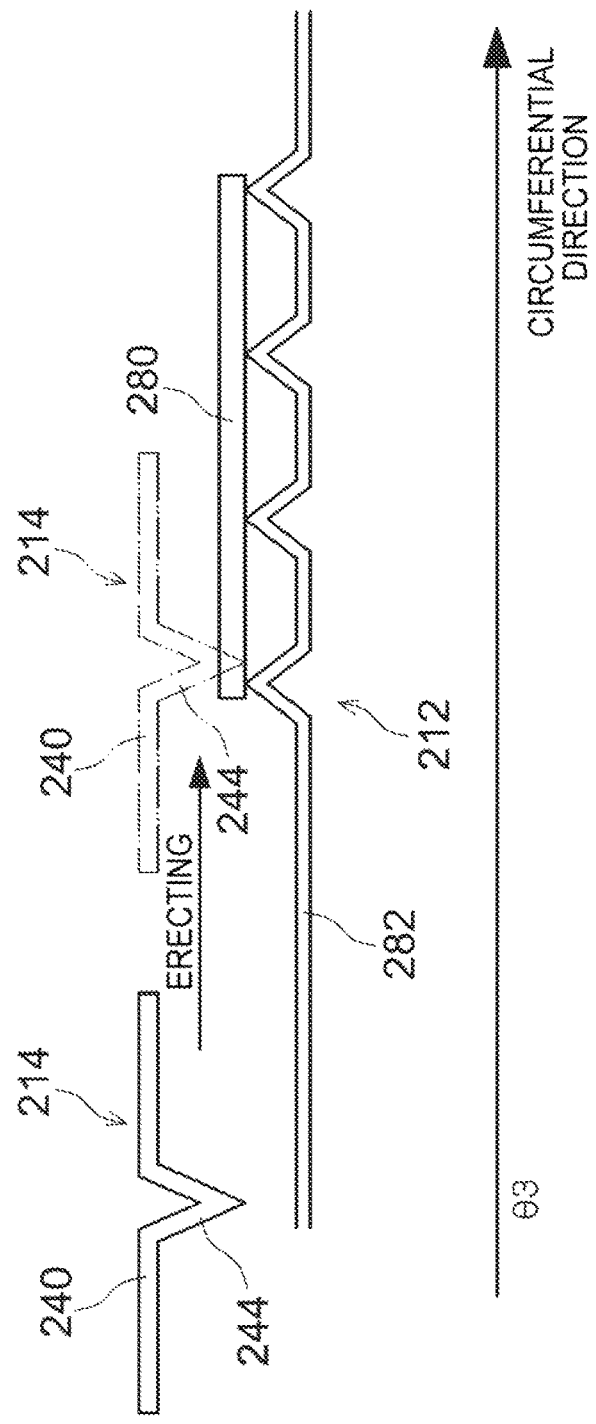
FIG. 24 is a diagram illustrating a modified example of a fixed part of the locking mechanism, and is a diagram where a friction plate is disposed instead of a locking pin.

In addition, the movement of the erecting operation lever 74 may be steplessly locked in the entire or partial range of the second operation range of the erecting operation lever 74. FIG. 24 illustrates a mode of the fixed part 212 in that case. The fixed part 212 illustrated in the figure includes: a friction plate 280 disposed along the movement direction of the movable part 214; and a plate spring 282 which supports the friction plate 280. Further, when the erecting operation lever 74 is operated in the second operation range, the locking projection 244 of the movable part 214 slidingly contacts with the friction plate 280 as a sliding contact member and is brought into pressure contact with the friction plate 280 by the plate spring 282 to generate the friction force. By this means, the movement of the erecting operation lever 74 is locked in continuous positions in the second operation range of the erecting operation lever 74. Here, in this mode, it is possible to use an arbitrary-shaped sliding contact member which slidingly contacts with the friction plate 280 and generates the friction force, instead of the locking projection 244. Moreover, the friction plate 280 may be disposed in a range (from angular position θ3a to angular position θ3max) corresponding to the whole of the second operation range or may be disposed in a partial range.

The fixed part 212 of the configurations illustrated in above-mentioned FIGS. 21 to 24 may not be provided only in a range (from angular position θ3a to angular position θ3max) corresponding to the second operation range of the erecting operation lever 74, but may be also provided in the first operation range (from angular position θ3min to angular position θ3a) of the erecting operation lever 74. Moreover, even in a mode in which the erecting operation lever 74 has only the first operation range, it is possible to provide the locking mechanism including the fixed part 212 having the configurations illustrated in FIGS. 21 to 24.

Next, explanation is given to a case where the locking mechanism 210 of the above-mentioned arbitrary embodiment is provided with a switching mechanism which varies a relative distance between the fixed part 212 and the movable part 214 to switch the fixed part 212 and the movable part 214 between an engagement state and a non-engagement state.

First, a mode to move the movable part 214 by the operation of the erecting operation lever 74 and vary the relative distance between the fixed part 212 and the movable part 214 is described.

Figure 25:
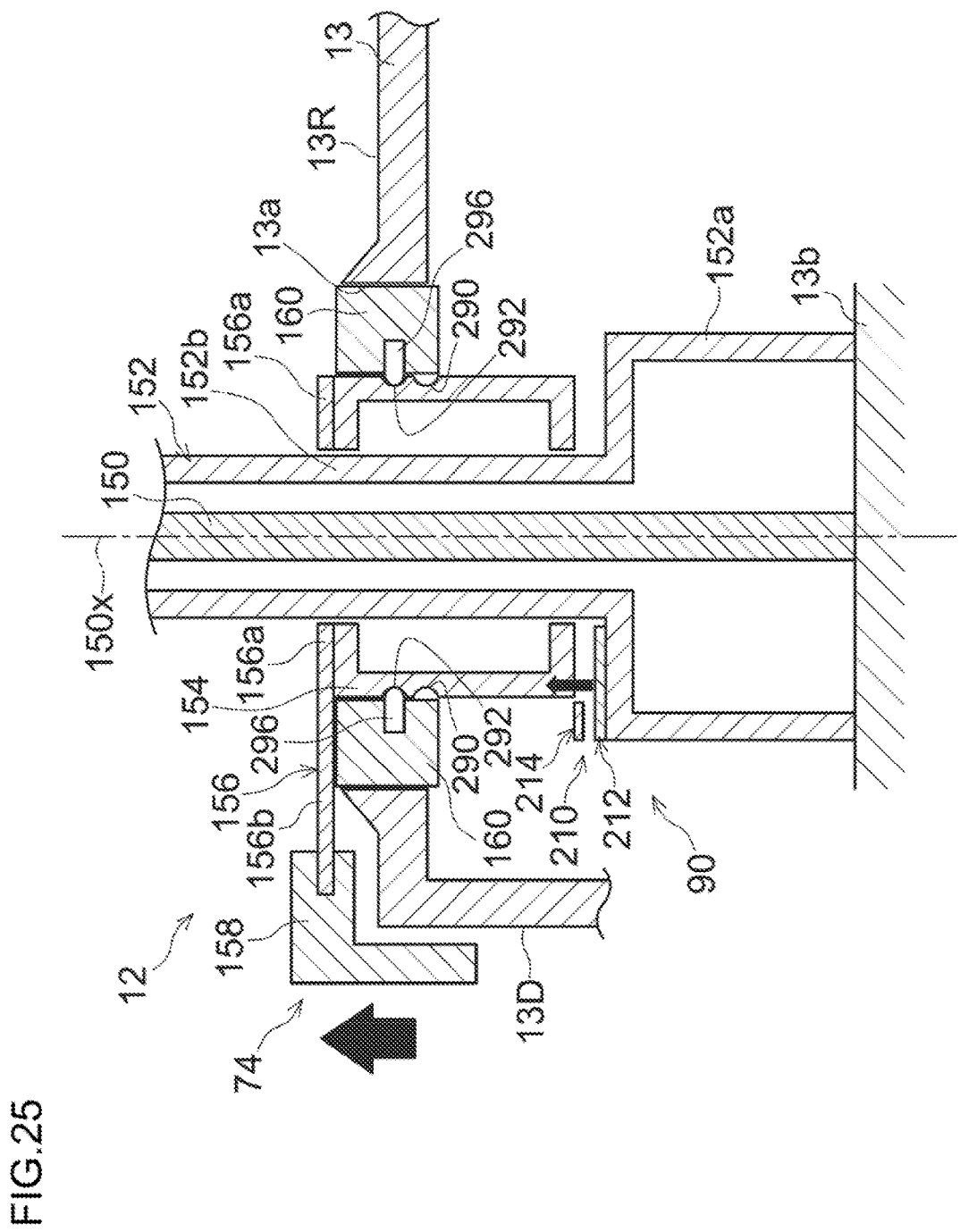
FIG. 25 is an image diagram illustrating a mechanism that makes a movable plate of the locking mechanism approach or move away from a stationary plate.

FIG. 25 illustrates the casing 13, the frame member 160, the erecting operation lever 74, the coupling member 156, the rotating drum 154, the fixing shaft 152 and the frame member 160 in FIG. 7, and the fixed part 212 and the movable part 214 of the locking mechanism 21 in FIG. 15. As illustrated in the figure, two grooves 290 and 292 are formed along the circumferential direction in the outer peripheral surface of the rotating drum 154. Meanwhile, ball plungers 296 are fixed in multiple positions in the inner peripheral surface of the annular frame member 160 fixed to the casing 13. Each ball plunger 296 has a ball which is urged toward its tip end direction in the tip end part and a part of which is exposed to the outside, and the ball exposed from the tip end part of the ball plunger 296 is engaged with any one of two grooves 290 and 292 of the rotating drum 154.

Moreover, the rotating drum 154 is supported so as to be movable in the direction of the axis 150x with respect to the fixing shaft 152, and is supported so as to be movable to a position in which the groove 290 is engaged with the ball plungers 296 and a position in which the groove 292 is engaged with the ball plungers 296. Thus, when the relative distance between the fixed part 212 and the movable part 214 of the locking mechanism 210 varies and the groove 292 of the rotating drum 154 is engaged with the ball plungers 296, the fixed part 212 and the movable part 214 of the locking mechanism 210 are engaged with each other to be in an engagement state. When the groove 290 of the rotating drum 154 is engaged with the ball plungers 296, the fixed part 212 and the movable part 214 of the locking mechanism 210 are not engaged with each other to be in a non-engagement state. Here, the engagement state in which the fixed part 212 and the movable part 214 of the locking mechanism 210 are engaged with each other and the non-engagement state in which they are not engaged mean, that, when the locking mechanism 210 is formed with a locking pin (220) and a locking projection (244) like the mode illustrated in FIG. 17, a state in which they are engaged (a state in which they can be engaged) and a state in which they are not engaged (a state in which they cannot be engaged). In a case where the locking mechanism 210 is formed with a friction plate (260) and a sliding contact member (locking pin 220) like the mode illustrated in FIG. 20, the engagement state and the non-engagement state mean that a state in which they slidingly contact with each other (a state in which they can slidingly contact with each other) and a state in which they do not slidingly contact with each other (a state in which they cannot slidingly contact with each other).

Figure 26:
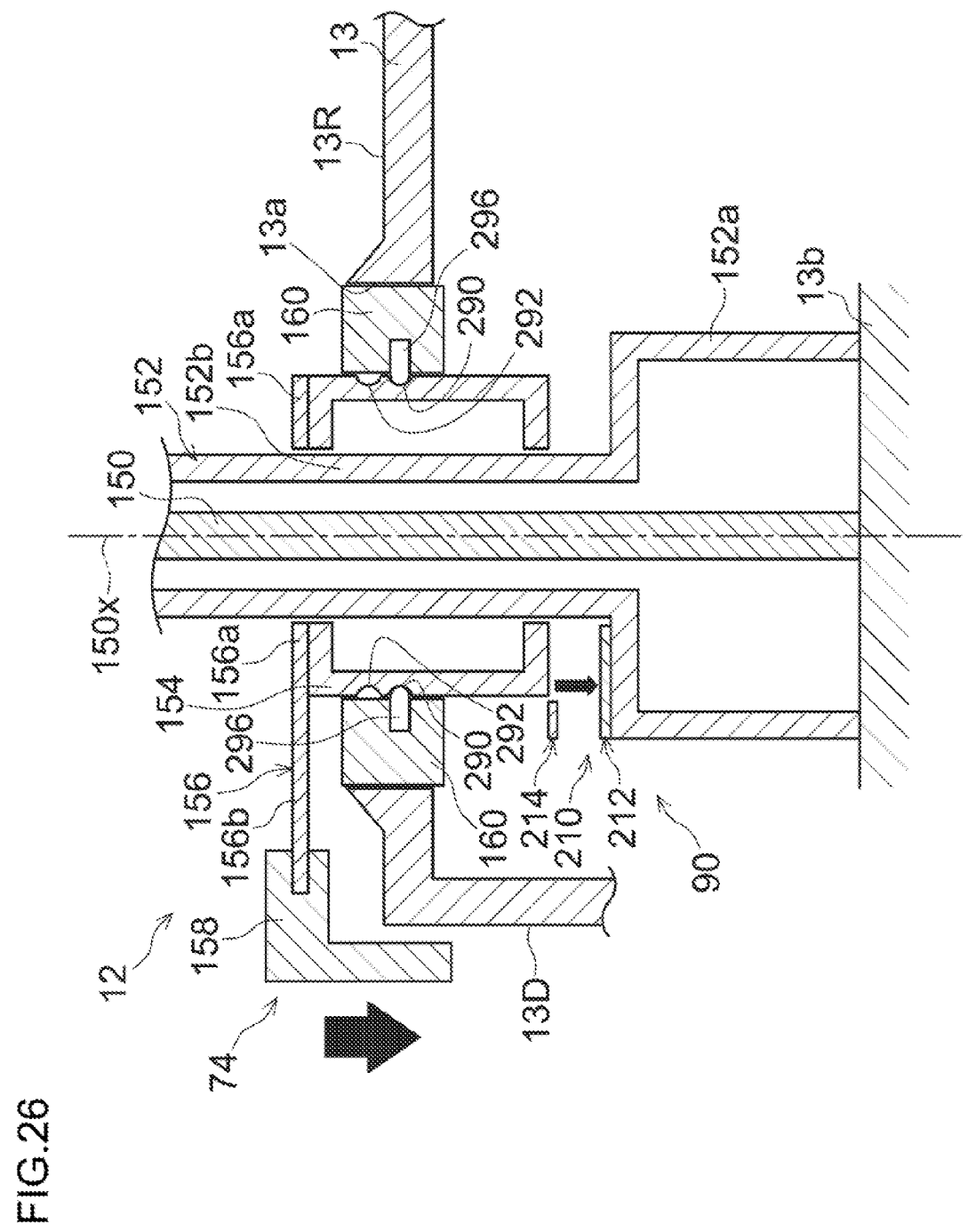
FIG. 26 is an image diagram illustrating the mechanism that makes the movable plate of the locking mechanism approach or move away from the stationary plate.

According to this, when the erecting operation lever 74 is operated to rotate and so on in order to erect the forceps elevator 60, if the erecting operation lever 74 is pushed out toward the distal end side of the main shaft 150, it is possible to move the rotating drum 154 to a position in which the groove 290 of the rotating drum 154 is engaged with the ball plungers 296 as illustrated in FIG. 26, to make the fixed part 212 and the movable part 214 of the locking mechanism 210 enter the non-engagement state. Thus, even in a case where the movement of the erecting operation lever 74 is locked by the locking mechanism 210, it is possible to operate the erecting operation lever 74 without applying a large amount of force. Moreover, it is possible to operate the erecting operation lever 74 without a load by the locking mechanism 210.

On the other hand, when the erecting operation lever 74 is pushed toward the proximal end side of the main shaft 150, it is possible to move the rotating drum 154 to a position in which the groove 292 of the rotating drum 154 is engaged with the ball plungers 296 like FIG. 25, and it is possible to make the fixed part 212 and the movable part 214 of the locking mechanism 210 enter the engagement state. Thus, it is possible to lock the movement of the erecting operation lever 74 by the locking mechanism 210.

Next, a mode in which the fixed part 212 is moved to vary the relative distance between the fixed part 212 and the movable part 214 is described.

Figure 27:
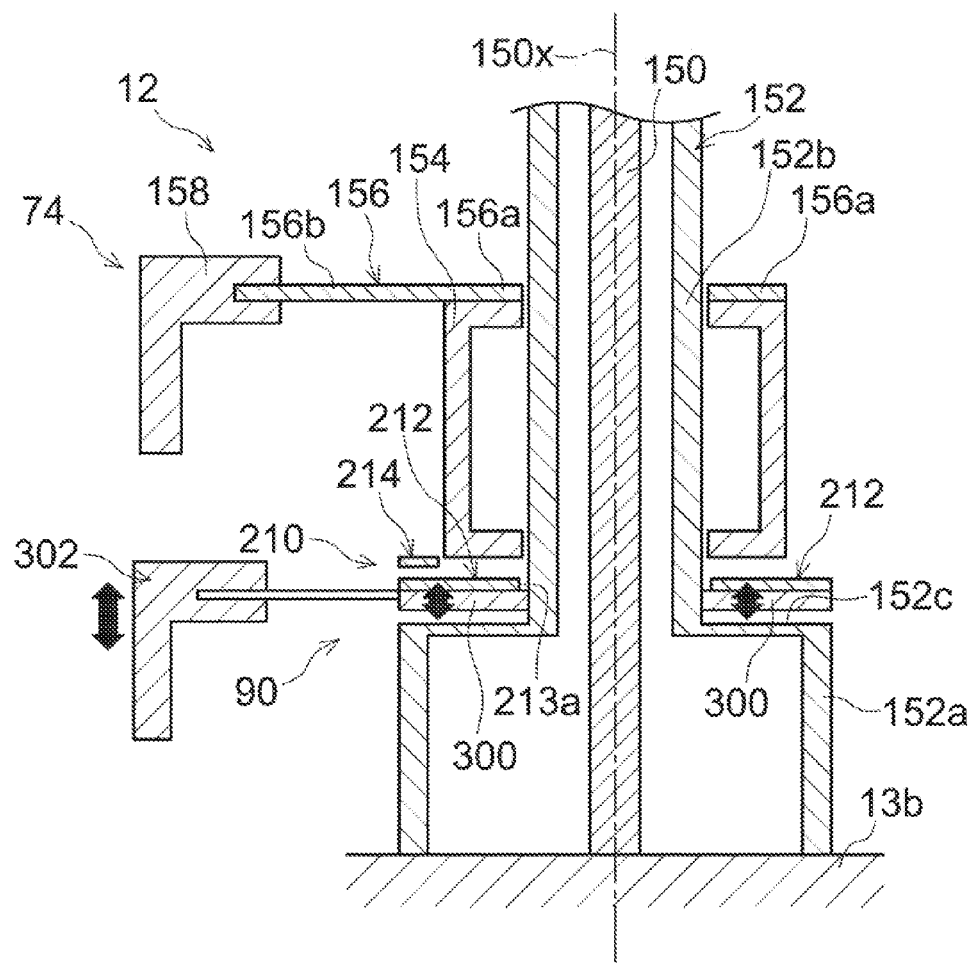
FIG. 27 is an image diagram illustrating the mechanism that makes the movable plate of the locking mechanism approach or move away from the stationary plate.

FIG. 27 illustrates the erecting operation lever 74, the coupling member 156, the rotating drum 154, the fixing shaft 152, and the fixed part 212 and the movable part 214 of the locking mechanism 21 in FIG. 15. As illustrated in the figure, the fixed part 212 of the locking mechanism 210 is fixed to a support member 300. The support member 300 is a circular plate member having a through hole in its central part. The fixing shaft 152 is inserted into the through hole and is disposed on the same axis as the main shaft 150. Moreover, a switching lever 302 is extended to the support member 300, and the switching lever 302 extends to the outside of an unillustrated casing (the above-mentioned casing 13). The system is configured such that: when the switching lever 302 is operated to move forward-and-backward along the axis 150x or to rotate around the axis 150x, the support member 300 moves forward and backward in a direction along the axis 150x by an unillustrated mechanism so as to vary the relative distance between the fixed part 212 and the movable part 214 of the locking mechanism 210. Thus, the fixed part 212 and the movable part 214 of the locking mechanism 210 can be switched between the engagement state and the non-engagement state, by the operation of the switching lever 302.

According to this, even in a case where the movement of the erecting operation lever 74 is locked by the locking mechanism 210, by making the fixed part 212 and the movable part 214 of the locking mechanism 210 enter the non-engagement state by the operation of the switching lever 302, it is possible to operate the erecting operation lever 74 without applying a large amount of force. Moreover, it is possible to operate the erecting operation lever 74 without a load applied by the locking mechanism 210.

On the other hand, by making the fixed part 212 and the movable part 214 of the locking mechanism 210 enter the engagement state by the operation of the switching lever 302, it is possible to lock the movement of the erecting operation lever 74 by the locking mechanism 210.

Next, the locking mechanism 210 of the above-mentioned arbitrary embodiment is described in a case where the amount of force (first amount of force) for the movement of the movable part 214 (locking projection 244) toward the erecting side and the amount of force (second amount of force) for the movement toward the reclining side are made different.

First, a mode in a case where the first amount of force is made less than the second amount of force is described.

As illustrated in FIG. 17 or the like, it is assumed that the locking mechanism 210 includes: the fixed part 212 having the chevron-shaped locking pin 220 as the first projection; and the movable part 214 having the chevron-shaped locking projection 244 as the second projection. Moreover, it is assumed that the locking projection 244 (movable part 214) includes: the slope surface 244u on the erecting side as the first surface which presses the locking pin 220 when the forceps elevator 60 is erected; and the slope surface 244d on the reclining side as the second surface which presses the locking pin 220 when the forceps elevator 60 is reclined.

Figure 28:
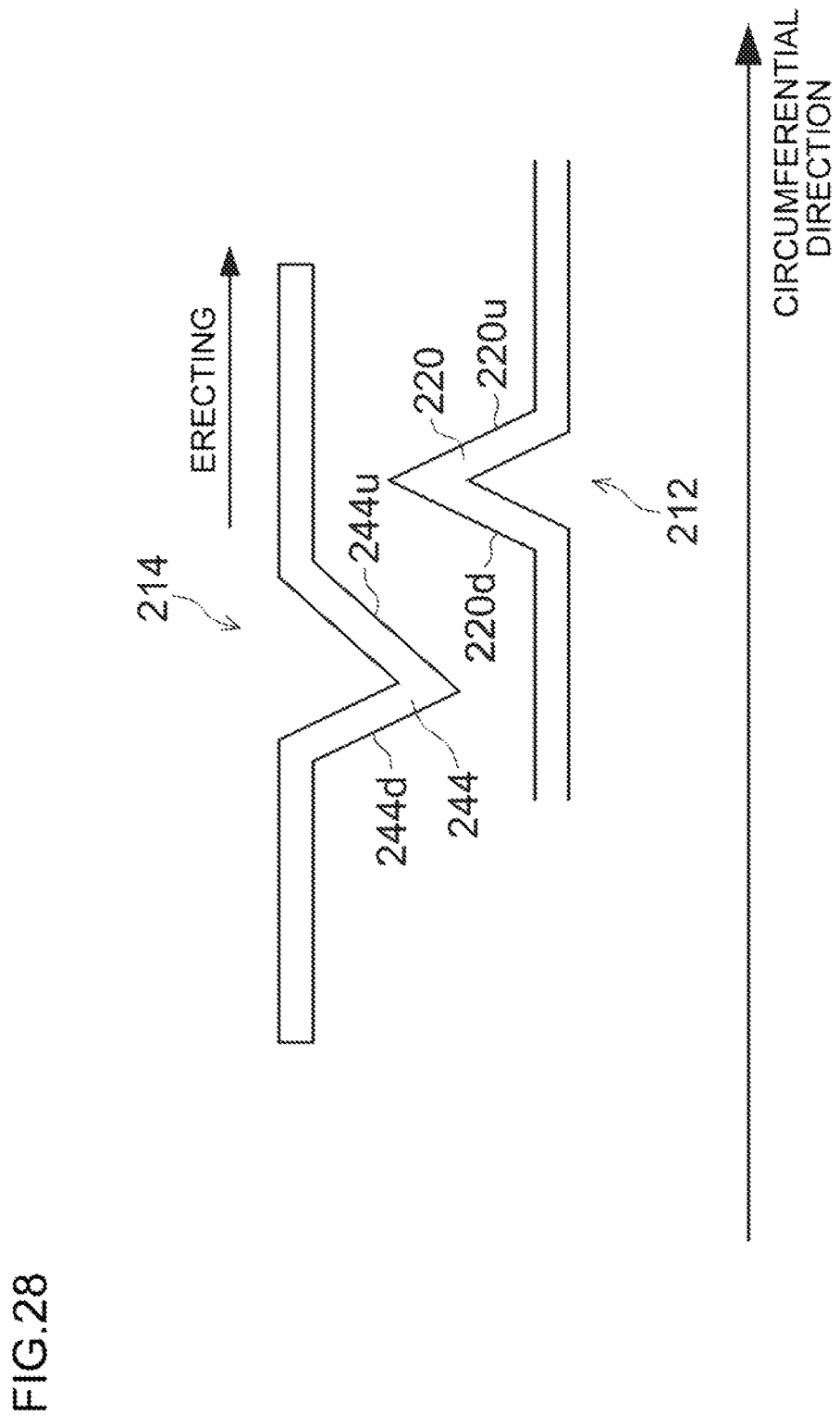
FIG. 28 is a diagram illustrating the shape of a locking projection of the movable part in a case where the amount of force required to the movement to the reclining side of the movable part in the locking mechanism is made greater than the amount of force required to the movement on the erecting side.

In such the mode, the locking projection 244 is formed into an asymmetrical chevron shape in which the slope angle of the slope surface 244u on the erecting side of the locking projection 244 (a slope angle with respect to the movement direction of the locking projection 244) is smaller than that of the slope surface 244d on the reclining side, as illustrated in FIG. 28. Thus, the locking projection 244 can easily ride across (get over) the locking pin 220 by the movement toward the erecting side, as compared to a case when the locking projection 244 rides across the locking pin 220 of the fixed part 212 by the movement toward the reclining side.

That is, if the amount of force when the locking projection 244 rides across the locking pin 220 by the movement toward the erecting side is assumed as the first amount of force and the amount of force when the locking projection 244 rides across the locking pin 220 by the movement toward the reclining side is assumed as the second amount of force, the second amount of force becomes greater than the first amount of force. Here, the first amount of force can be paraphrased as the amount of force required when the locking pin 220 rides across the slope surface 244u on the erecting side of the locking projection 244, and the second amount of force can be paraphrased as the amount of force required when the locking pin 200 rides across the slope surface 244d on the reclining side of the locking projection 244.

Moreover, if the amount of force applied to the erecting operation lever 74 when the erecting operation lever 74 is operated in a direction in which the forceps elevator 60 is erected is assumed as the first operation amount of force and the amount of force applied to the erecting operation lever 74 when the erecting operation lever 74 is operated in a direction in which the forceps elevator 60 is reclined is assumed as the second operation amount of force, by adopting the locking mechanism 210 in this mode, the first operation amount of force becomes less than the second operation amount of force.

Figure 29:
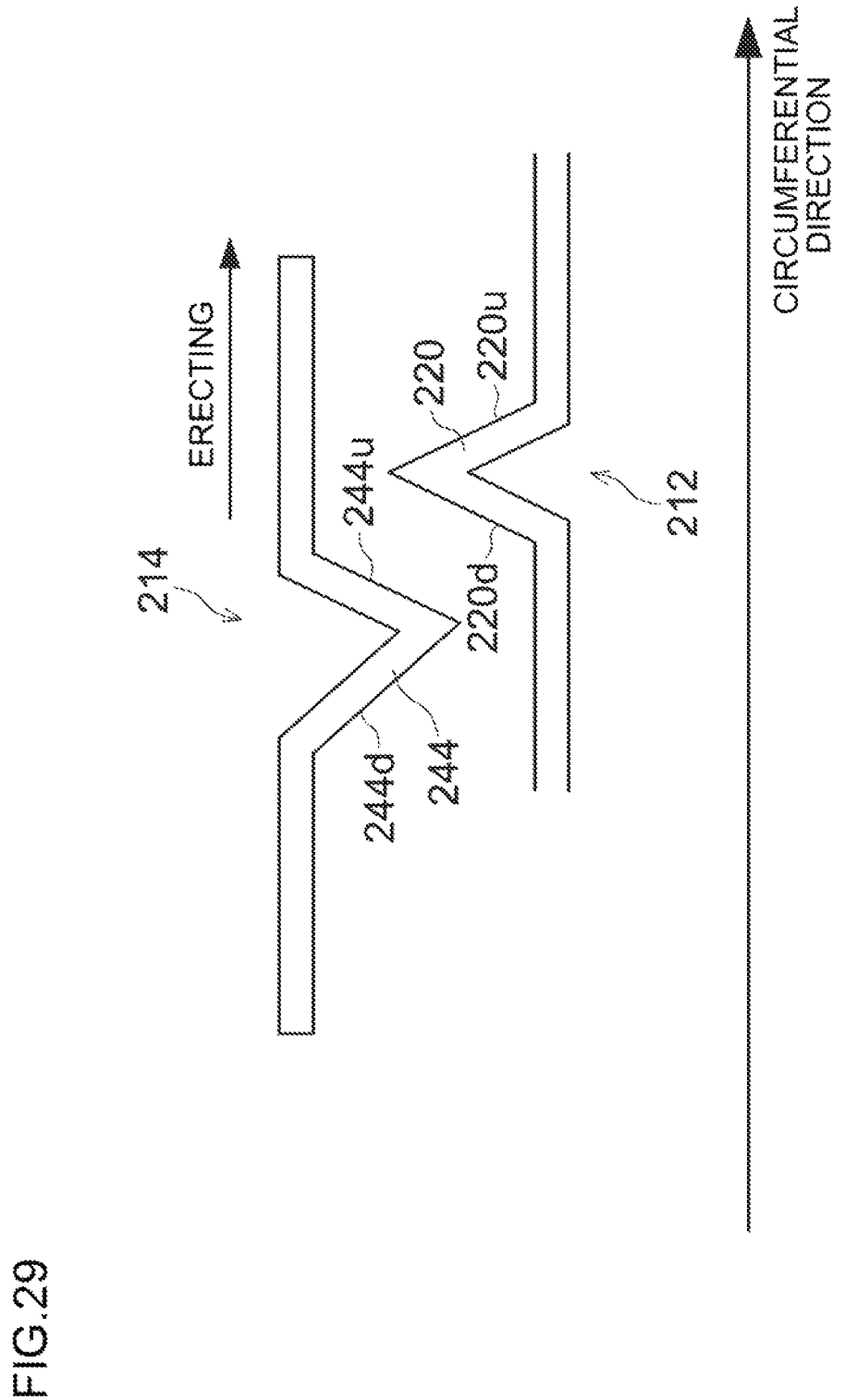
FIG. 29 is a diagram illustrating the shape of a locking projection of a movable part in a case where the amount of force required to the movement to the reclining side of the movable part in the locking mechanism is made greater than the amount of force required to the movement on the erecting side.

By contrast, in a case where the first amount of force is made greater than the second amount of force, the slope angle of the slope surface 244d on the reclining side of the locking projection 244 is smaller than the slope surface 244u on the erecting side as illustrated in FIG. 29.

In this case, the second operation amount of force applied to the erecting operation lever 74 when the forceps elevator 60 is reclined becomes less than the first operation amount of force applied to the erecting operation lever 74 when the forceps elevator 60 is erected.

For example, in the case of the endoscope 1 including the ultrasonic transducer 50 of the present embodiment, for example, as illustrated in FIG. 11, the endoscope 1 is used when tissue sampling is performed by puncturing target site T with the puncture needle 180. At this time, as the puncture needle 180, there is a case where the one having a large bending stiffness is used. In that case, a large force is applied to the movement of the locking projection 244 toward the reclining side. Therefore, it is desirable to mitigate an operation load by increasing the second amount of force for locking the movement of the erecting operation lever 74 toward the reclining side against such the force and decreasing the first amount of force for locking the movement of the erecting operation lever 74 toward the erecting side. That is, it is desirable to make the second amount of force greater than the first amount of force as illustrated in FIG. 28.

On the other hand, in an endoscope equipped with a side-view-type endoscope observing device including an illuminating unit and an observing unit in the distal end part of an insertion part like duodenoscopy, in a case where a guide wire is used in the procedure of ERCP, it is considered that the locking to the movement of the erecting operation lever 74 toward the reclining side by the above mentioned locking mechanism 210 is used as a lock of the guide wire. In that case, when a position in which the guide wire is greatly bent by the forceps elevator 60 is assumed as a lock position, if a treatment tool having a low flexibility is used, there is a possibility that the treatment tool is damaged at the time when locked also in such the lock position. Therefore, in order to mitigate an operator's operation load, it is desirable that: the first amount of force for locking the movement of the erecting operation lever 74 toward the erecting side is increased so as to notify the operator that the operation range enters the lock position of the guide wire, that is, the range is not in a normal operation range; and the second amount of force for locking the movement of the erecting operation lever 74 toward the reclining side is decreased. That is, it is desirable to make the first amount of force greater than the second amount of force as illustrated in FIG. 29.

Here, FIGS. 28 and 29 illustrate only one locking pin 220 in the fixed part 212, but it is possible to apply the mode illustrated in FIGS. 28 and 29 even to a mode in which a plurality of locking pins 220 (locking pin 220e) are provided like the mode illustrated in FIGS. 21 and 22.

Moreover, these modes are effective even when a locking mechanism similar to the above-mentioned embodiment is applied to the first operation range in a case where the erecting operation lever 74 has only the first operation range.

Figure 30:
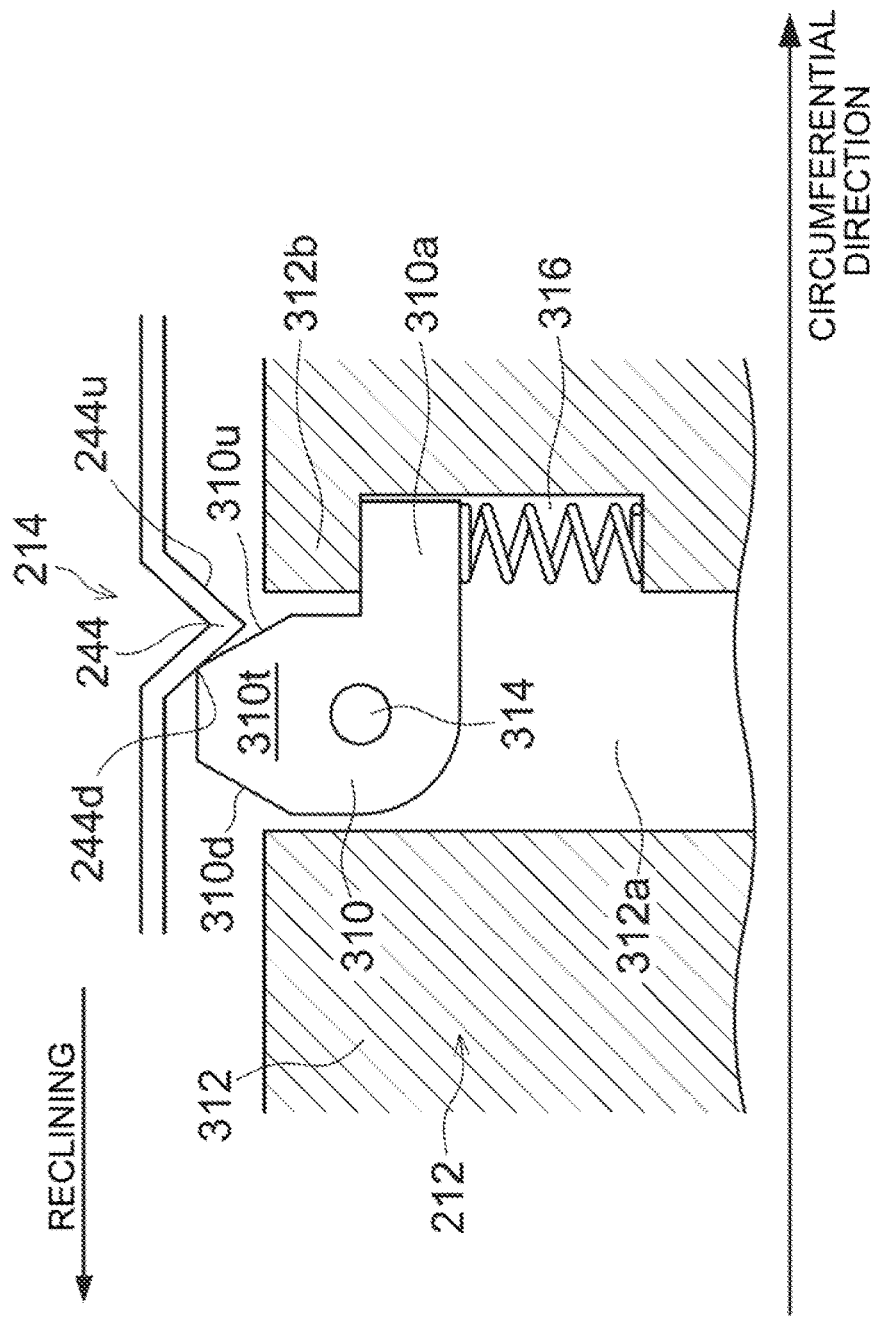
FIG. 30 is a diagram illustrating the configuration of a locking pin of a movable part in a case where the amount of force required to the movement to the reclining side of the movable part in the locking mechanism is made greater than the amount of force required to the movement on the erecting side.

Moreover, it is possible to adopt a configuration like FIG. 30, as another mode of a locking mechanism in which the first amount of force and the second amount of force are made different. In the locking mechanism 210 in the figure, the movable part 214 has the chevron-shaped locking projection 244 as the first projection, as illustrated in FIG. 17 or the like.

Meanwhile, the fixed part 212 has a support member 312 in which a concave part 312a is formed, and a locking pin 310, as a second projection, is rotatably supported in the concave part 312a by a shaft 314.

The locking pin 310 is disposed such that a part of the lock pin 301 projects from the concave part 312a. In the part (projection part 310t) projecting from the concave part, there are formed: a first surface 310d which presses the locking projection 244 when the forceps elevator 60 is erected (on which the slope surface 244u on the erecting side of the locking projection 244 abuts); and a second surface 310u which presses the locking projection 244 when the forceps elevator 60 is reclined (on which the slope surface 244d on the reclining side of the locking projection 244 abuts).

Moreover, the locking pin 310 is provided with a convex part 310a. The convex part 310a is urged to the anti-clockwise direction (a direction in which the projection part 310t inclines toward the reclining side) centering on the shaft 314 by a spring 316 in the concave part 312a in the figure. Meanwhile, the convex part 310a is inhibited from rotating in the anti-clockwise direction in the figure by abutting on a locking part 312b which is protrusively formed in (formed so as to protrude from) the opening part of the concave part 312a.

Accordingly, when the movable part 214 moves toward the reclining side as illustrated in the figure, the slope surface 244d on the reclining side of the locking projection 244 abuts on the second surface 310u on the erecting side of the locking pin 310. At this time, the projection part 310t of the locking pin 310 is pressed toward the reclining side and the locking pin 310 is pressed toward the anti-clockwise direction in the figure. However, since the rotation in the anti-clockwise direction is inhibited by the locking part 312b, the rotation amount (second rotation amount) of the locking pin 310 at this time is small.

Figure 31:
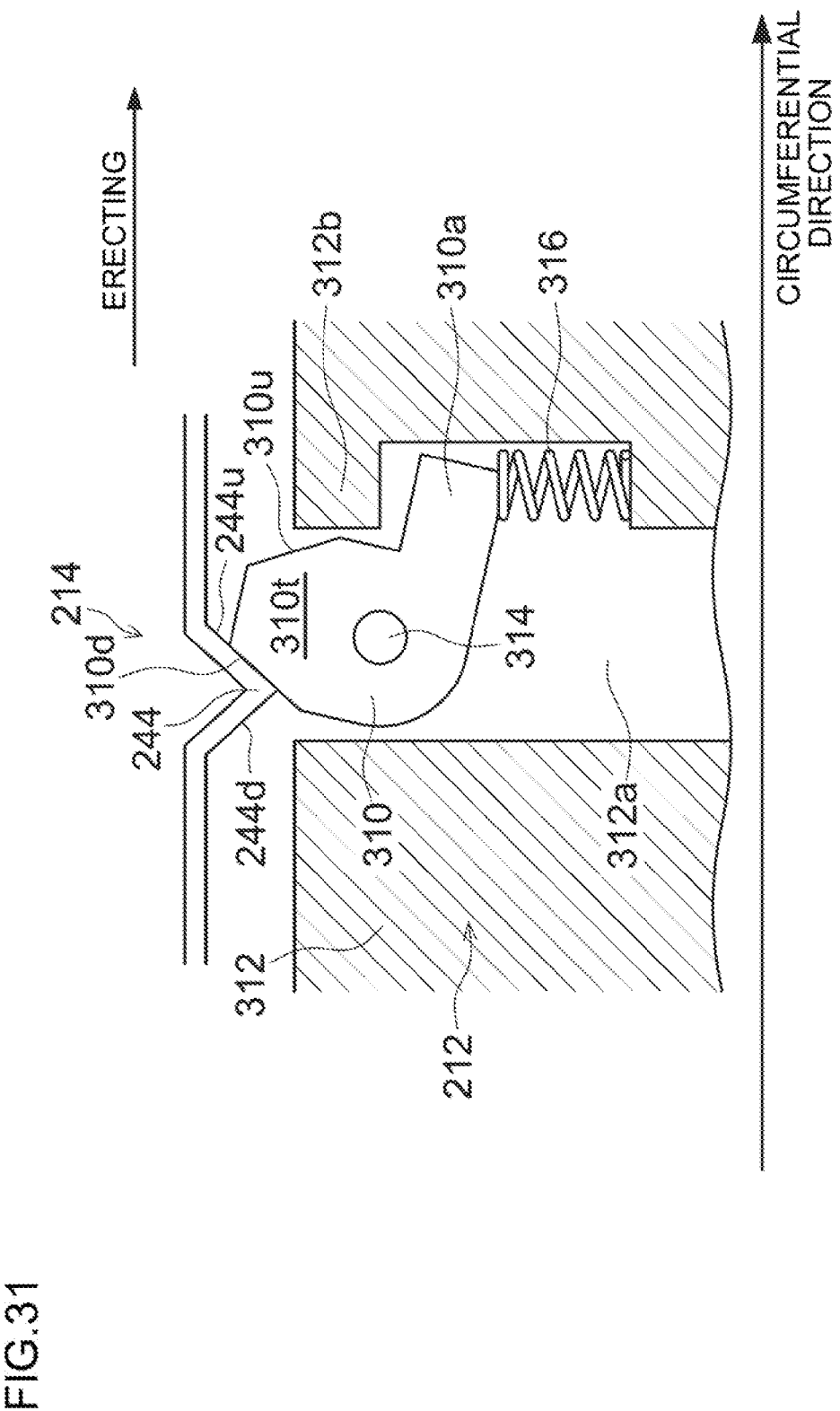
FIG. 31 is a diagram illustrating a state where the locking pin of the fixed part in FIG. 30 rotates.

On the other hand, when the erecting operation lever 74 is operated toward the erecting side and the movable part 214 moves toward the erecting side, the slope surface 244u on the erecting side of the locking projection 244 abuts on the first surface 310d on the reclining side of the locking pin 310 as illustrated in FIG. 31. Thus, the projection part 310t of the locking pin 310 is pressed toward the erecting side and the locking pin 310 is pressed toward the clockwise direction in the figure. Since the rotation at this time is not prohibited by the locking part 312b, the rotation amount of the locking pin 310 (first rotation amount) becomes greater than the second rotation amount.

Therefore, the height of the locking pin 310 which the locking projection 244 rides across becomes smaller when the erecting operation lever 74 is operated toward the erecting side.

That is, if the amount of force when the locking projection 244 rides across the first surface 310d on the reclining side of the locking pin 310 by the movement toward the erecting side is assumed as the first amount of force and the amount of force when the locking projection 244 rides across the second surface 310u on the erecting side of the locking pin 310 by the movement toward the reclining side is assumed as the second amount of force, the second amount of force becomes greater than the first amount of force.

In order to make the first amount of force greater than the second amount of force by a configuration similar to FIGS. 30 and 31, it only has to adopt a configuration in which the configuration of the fixed part 212 in FIG. 30 is horizontally reversed (right-and-left reversed).

In the locking mechanism 210 illustrated in above-mentioned FIGS. 28 to 31, the configuration can be modified so that the configuration of the projection disposed in the fixed part 212 and the configuration of the projection disposed in the movable part 214 are replaced with each other. That is, it is possible to adopt a configuration in which any one of the first projection and the second projection is disposed in the fixed part 212 and the other one is disposed in the movable part 214.

As mentioned above, the locking mechanism 210 of the above-mentioned embodiment is not restricted to an endoscope of a specific type, and it is applicable to an endoscope of an arbitrary type.

What is claimed is:

1. An endoscope apparatus comprising:
   an insertion part configured to be inserted into a body; an operation part continuously provided on a proximal end side of the insertion part;
   a forceps elevator which is erectably provided to a distal end part of the insertion part, has an erecting motion range from a minimum angular position where the forceps elevator is most reclined to a maximum angular position where the forceps elevator is most erected, and is configured to guide a treatment tool led out from the distal end part;
   an operation wire coupled at one end with the forceps elevator and which is inserted into the insertion part; and
   an erecting operation lever provided to the operation part, coupled to the other end of the operation wire, and configured to operate the operation wire to erect the forceps elevator;
   a first elevator restricting surface configured to restrict the forceps elevator to the minimum angular position in the erecting motion range;
   a second elevator restricting surface configured to restrict the forceps elevator to the maximum angular position in the erecting motion range;
   a first operation lever restricting surface provided in the operation part, and configured to restrict the erecting operation lever to one end position on a side the forceps elevator is reclined in an entire operating range where the erecting operation lever is operable; and
   a second operation lever restricting surface provided in the operation part, and configured to restrict the erecting operation lever to the other end position on a side the forceps elevator is erected in the entire operating range where the erecting operation lever is operable,
   wherein an index is disposed on the operation part between the operation part and the erecting operation lever such that the index is entirely shielded by the erecting operation lever when the forceps elevator is in the minimum angular position, and such that the index is exposed when the forceps elevator is in a position in which the forceps elevator is erected from the minimum angular position,
   wherein, when an intermediate position is defined between the one end position and the other end position in the entire operating range of the erecting operation lever, the erecting operation lever has: a first operating range being a range between the one end position and the intermediate position; and a second operating range being a range between the intermediate position and the other end position,
   wherein, the operation wire has a length such that the forceps elevator is movable from the minimum angular position to the maximum angular position when the erecting operation lever is operated from the one end position to the intermediate position in the first operating range in a state where the treatment tool is not led out from the distal end part,
   wherein, the second operating range is a range enabling to position the forceps elevator at the maximum angular position by operating the erecting operation lever from the intermediate position toward the other end position, when the forceps elevator is positioned at an angular position smaller than the maximum angular position even though the erecting operation lever is operated and reaches the intermediate position in a state where the treatment tool is led out from the distal end part.

2. The endoscope apparatus according to claim 1, wherein, when an entire operation range of the erecting operation lever is formed with the first operation range and the second operation range, the first operation range is 40% or more and 70% less of the entire operation range of the erecting operation lever.

3. The endoscope apparatus according to claim 1, wherein the operation part includes an index configured to identify whether an operation range of the erecting operation lever is in the first operation range or in the second operation range.

4. The endoscope apparatus according to claim 1, further comprising a bending operation knob which is rotatably arranged to the operation part and is configured to perform a bending operation of a bending part provided on a distal end side of the insertion part,
   wherein the erecting operation lever is rotatably arranged on a same axis as a rotation axis of the bending operation knob.

5. The endoscope apparatus according to claim 1, wherein the operation part includes a stopper configured to be relatively movable between the first operation lever restricting surface and the second operation lever restricting surface in accordance with operation of the erecting operation lever,
   wherein the stopper restricts the erecting operation lever to the one end position on the side the forceps elevator is reclined in the entire operating range when the stopper abuts against the first operation lever restricting surface, and
   wherein, in a state where the treatment tool is not led out from the distal end part, when the erecting operation lever is operated from the one end position toward the other end position, the second elevator restricting surface and the second operation lever restricting surface satisfy a positional relationship in which the second elevator restricting surface restricts the forceps elevator to the maximum angular position before the second operation lever restricting surface restricts the erecting operation lever to the other end position.

6. The endoscope apparatus according to claim 5, wherein
the stopper is movable along a groove provided in the operation part, and
the first and second operation lever restricting surfaces are both end surfaces of the groove.

* * * * *